United States Patent
Cornell-Bell

(10) Patent No.: US 11,360,101 B2
(45) Date of Patent: Jun. 14, 2022

(54) IN VITRO METHOD FOR DIAGNOSING CENTRAL NERVOUS SYSTEM INJURY

(71) Applicant: Perseus Science Group LLC, Old Lyme, CT (US)

(72) Inventor: Ann H. Cornell-Bell, Westbrook, CT (US)

(73) Assignee: Perseus Science Group LLC, Old Lyme, CT (US)

(*) Notice: Subject to any disclaimer, the term of this patent is extended or adjusted under 35 U.S.C. 154(b) by 0 days.

(21) Appl. No.: 17/503,441

(22) Filed: Oct. 18, 2021

(65) Prior Publication Data

US 2022/0057411 A1    Feb. 24, 2022

Related U.S. Application Data

(63) Continuation of application No. PCT/US2021/016740, filed on Feb. 5, 2021.

(60) Provisional application No. 62/970,769, filed on Feb. 6, 2020.

(51) Int. Cl.
  *G01N 33/553* (2006.01)
  *G01N 33/68* (2006.01)
  *C07K 16/40* (2006.01)
  *C07K 16/18* (2006.01)

(52) U.S. Cl.
  CPC ......... *G01N 33/6893* (2013.01); *C07K 16/40* (2013.01); *G01N 33/6857* (2013.01); *C07K 16/18* (2013.01); *C07K 2317/565* (2013.01); *G01N 2800/2871* (2013.01)

(58) Field of Classification Search
  None
  See application file for complete search history.

(56) References Cited

U.S. PATENT DOCUMENTS

| 6,268,223 B1 | 7/2001 | Cornell-Bell et al. |
| 2007/0005261 A1 | 1/2007 | Serena et al. |
| 2009/0297513 A1 | 12/2009 | Garcia-Martinez et al. |

FOREIGN PATENT DOCUMENTS

| WO | 2000/053218 A1 | 9/2000 |
| WO | 0116599 A1 | 3/2001 |
| WO | 2018/118780 A1 | 6/2018 |

OTHER PUBLICATIONS

Sep. 1, 20210—(WO) International Search Report & Written Opinion—App. No. PCT/US2021/016740.

(Continued)

*Primary Examiner* — Aurora M Fontainhas
(74) *Attorney, Agent, or Firm* — Banner & Witcoff, Ltd.

(57) ABSTRACT

The present invention provides a highly sensitive in vitro method for diagnosing injury to the central nervous system (CNS), such as a traumatic brain injury (TBI) or stroke. The method involves contacting a sample of blood from a subject suspected of suffering a CNS injury event with at least one antibody capable of detecting a proteolytic fragment of the biomarker Protein Kinase C, gamma isoform (PKCg or PKCγ), which fragment corresponds to a proteolytic fragment of PKCg formed in the excitotoxic environment resulting from neuronal damage. Also disclosed are novel anti-PKCg antibodies useful in the diagnostic methods of the invention to provide diagnosis of CNS injury with essentially 100% accuracy.

6 Claims, 12 Drawing Sheets

Specification includes a Sequence Listing.

(56) References Cited

OTHER PUBLICATIONS

Zhang et al., "PKCg promotes axonal remodeling in the corticospinal tract via GSK3b/b-catenin signaling after traumatic brain injury," Scientific Reports, vol. 19, Article No. 17078, pp. 1-16 (Nov. 19, 2019).

Immuno American anti-PKC gamma antibody product page (Copyright 2018). Retrieved from the internet <URL: https://immunoamerican.com/shop/ols/products/anti-pkc-gamma-antibody> on Jun. 8, 2021.

SEQUENCE LISTING

<160> NUMBER OF SEQ ID NOS: 38

<210> SEQ ID NO 1
<211> LENGTH: 697
<212> TYPE: PRT
<213> ORGANISM: Homo sapiens

<400> SEQUENCE: 1

```
Met Ala Gly Leu Gly Pro Gly Val Gly Asp Ser Glu Gly Gly Pro Arg
1               5                   10                  15

Pro Leu Phe Cys Arg Lys Gly Ala Leu Arg Gln Lys Val Val His Glu
            20                  25                  30

Val Lys Ser His Lys Phe Thr Ala Arg Phe Phe Lys Gln Pro Thr Phe
        35                  40                  45

Cys Ser His Cys Thr Asp Phe Ile Trp Gly Ile Gly Lys Gln Gly Leu
    50                  55                  60

Gln Cys Gln Val Cys Ser Phe Val Val His Arg Arg Cys His Glu Phe
65                  70                  75                  80

Val Thr Phe Glu Cys Pro Gly Ala Gly Lys Gly Pro Gln Thr Asp Asp
                85                  90                  95

Pro Arg Asn Lys His Lys Phe Arg Leu His Ser Tyr Ser Ser Pro Thr
            100                 105                 110

Phe Cys Asp His Cys Gly Ser Leu Leu Tyr Gly Leu Val His Gln Gly
        115                 120                 125

Met Lys Cys Ser Cys Cys Glu Met Asn Val His Arg Arg Cys Val Arg
    130                 135                 140

Ser Val Pro Ser Leu Cys Gly Val Asp His Thr Glu Arg Arg Gly Arg
145                 150                 155                 160

Leu Gln Leu Glu Ile Arg Ala Pro Thr Ala Asp Glu Ile His Val Thr
                165                 170                 175

Val Gly Glu Ala Arg Asn Leu Ile Pro Met Asp Pro Asn Gly Leu Ser
            180                 185                 190

Asp Pro Tyr Val Lys Leu Lys Leu Ile Pro Asp Pro Arg Asn Leu Thr
        195                 200                 205

Lys Gln Lys Thr Arg Thr Val Lys Ala Thr Leu Asn Pro Val Trp Asn
    210                 215                 220
```

-continued

```
Glu Thr Phe Val Phe Asn Leu Lys Pro Gly Asp Val Glu Arg Arg Leu
225                 230                 235                 240

Ser Val Glu Val Trp Asp Trp Asp Arg Thr Ser Arg Asn Asp Phe Met
            245                 250                 255

Gly Ala Met Ser Phe Gly Val Ser Glu Leu Leu Lys Ala Pro Val Asp
        260                 265                 270

Gly Trp Tyr Lys Leu Leu Asn Gln Glu Glu Gly Glu Tyr Tyr Asn Val
    275                 280                 285

Pro Val Ala Asp Ala Asp Asn Cys Ser Leu Leu Gln Lys Phe Glu Ala
290                 295                 300

Cys Asn Tyr Pro Leu Glu Leu Tyr Glu Arg Val Arg Met Gly Pro Ser
305                 310                 315                 320

Ser Ser Pro Ile Pro Ser Pro Ser Pro Thr Asp Pro Lys Arg
            325                 330                 335

Cys Phe Phe Gly Ala Ser Pro Gly Arg Leu His Ile Ser Asp Phe Ser
        340                 345                 350

Phe Leu Met Val Leu Gly Lys Gly Ser Phe Gly Lys Val Met Leu Ala
    355                 360                 365

Glu Arg Arg Gly Ser Asp Glu Leu Tyr Ala Ile Lys Ile Leu Lys Lys
370                 375                 380

Asp Val Ile Val Gln Asp Asp Val Asp Cys Thr Leu Val Glu Lys
385                 390                 395                 400

Arg Val Leu Ala Leu Gly Gly Arg Gly Pro Gly Gly Arg Pro His Phe
            405                 410                 415

Leu Thr Gln Leu His Ser Thr Phe Gln Thr Pro Asp Arg Leu Tyr Phe
        420                 425                 430

Val Met Glu Tyr Val Thr Gly Gly Asp Leu Met Tyr His Ile Gln Gln
    435                 440                 445

Leu Gly Lys Phe Lys Glu Pro His Ala Ala Phe Tyr Ala Ala Glu Ile
450                 455                 460

Ala Ile Gly Leu Phe Phe Leu His Asn Gln Gly Ile Ile Tyr Arg Asp
465                 470                 475                 480

Leu Lys Leu Asp Asn Val Met Leu Asp Ala Glu Gly His Ile Lys Ile
            485                 490                 495

Thr Asp Phe Gly Met Cys Lys Glu Asn Val Phe Pro Gly Thr Thr Thr
        500                 505                 510

Arg Thr Phe Cys Gly Thr Pro Asp Tyr Ile Ala Pro Glu Ile Ile Ala
    515                 520                 525

Tyr Gln Pro Tyr Gly Lys Ser Val Asp Trp Trp Ser Phe Gly Val Leu
530                 535                 540

Leu Tyr Glu Met Leu Ala Gly Gln Pro Pro Phe Asp Gly Glu Asp Glu
545                 550                 555                 560

Glu Glu Leu Phe Gln Ala Ile Met Glu Gln Thr Val Thr Tyr Pro Lys
            565                 570                 575

Ser Leu Ser Arg Glu Ala Val Ala Ile Cys Lys Gly Phe Leu Thr Lys
        580                 585                 590

His Pro Gly Lys Arg Leu Gly Ser Gly Pro Asp Gly Glu Pro Thr Ile
    595                 600                 605

Arg Ala His Gly Phe Phe Arg Trp Ile Asp Trp Glu Arg Leu Glu Arg
610                 615                 620

Leu Glu Ile Pro Pro Pro Phe Arg Pro Arg Pro Cys Gly Arg Ser Gly
625                 630                 635                 640

Glu Asn Phe Asp Lys Phe Phe Thr Arg Ala Ala Pro Ala Leu Thr Pro
```

```
                    645                 650                 655

Pro Asp Arg Leu Val Leu Ala Ser Ile Asp Gln Ala Asp Phe Gln Gly
            660                 665                 670

Phe Thr Tyr Val Asn Pro Asp Phe Val His Pro Asp Ala Arg Ser Pro
        675                 680                 685

Thr Ser Pro Val Pro Val Pro Val Met
    690                 695

<210> SEQ ID NO 2

<400> SEQUENCE: 2

000

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Ser Leu Asn Tyr Tyr Ala
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Thr Ser Asp Thr Thr
1               5

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ser Gly Gly Ser Thr Thr Ser Pro Ala Leu
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Val Trp Ser Lys Asn Tyr
1               5

<210> SEQ ID NO 7
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 7

Ser Ala Ser
1

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Gly Ser Tyr Asp Cys Arg Ser Ala Asp Cys Trp Thr
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Phe Ser Leu Ser Ser Tyr Ala
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Ile Ser Gly Gly Ser Ala
1               5

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Arg Ala Lys Ser Gly Thr Tyr Thr Gly Asp Tyr Phe Thr Leu
1               5                   10                  15

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Ser Ile Gly Asn Ala
1               5
```

```
<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ala Ser
1

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Tyr Val Gly Ser Arg Ser Thr Gly Tyr Asn Val
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Phe Thr Leu Thr Thr Tyr Trp
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Leu Thr Gly Ser Gly Ser Thr
1               5

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Arg Tyr Gly Gly Asp Ala Thr Tyr Asn Glu Asn Leu
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 18

Gln Ser Val Tyr Asn Asn Arg
1               5

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Val Ser
1

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Gly Gly Tyr Asp Cys Ala Ser Ala Asp Cys Tyr Ala
1               5                   10

<210> SEQ ID NO 21
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Thr Pro Leu Ala Leu Thr Cys Thr Val Ser Gly Phe Ser Leu Asn
            35                  40                  45

Tyr Tyr Ala Met Asn Trp Val Arg Gln Ala Pro Val Lys Gly Leu Glu
        50                  55                  60

Trp Ile Gly Val Ile Thr Ser Asp Thr Thr Tyr Tyr Ala Ser Trp Ala
65                  70                  75                  80

Lys Gly Arg Phe Thr Ile Ser Lys Thr Ser Thr Thr Val Glu Leu Gln
                85                  90                  95

Ile Thr Ser Pro Thr Thr Glu Asp Thr Ala Thr Tyr Phe Cys Ala Ser
            100                 105                 110

Gly Gly Ser Thr Thr Ser Pro Ala Leu Trp Gly Gln Gly Thr Leu Val
        115                 120                 125

Thr Val Ser Ser
    130

<210> SEQ ID NO 22
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 22

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Ser Thr Val Thr Ile Asn Cys Gln Ala Ser
        35                  40                  45

Gln Ser Val Trp Ser Lys Asn Tyr Leu Ser Trp Phe Gln Gln Lys Pro
    50                  55                  60

Gly Gln Pro Pro Lys Gln Leu Ile Tyr Ser Ala Ser Thr Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Leu Gly Ser Tyr Asp Cys Arg Ser Ala Asp Cys Trp Thr Phe Gly Gly
        115                 120                 125

Gly Thr Glu Val Val Val Lys
    130                 135

<210> SEQ ID NO 23
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Leu Ser Arg Asn Ala Val Ser Trp Val Arg Gln Ala Pro Gly Lys Gly
    50                  55                  60

Leu Glu Trp Thr Gly Ile Ile Phe Gly Asp Ala Lys Thr Tyr Tyr Ala
65                  70                  75                  80

Ser Trp Ala Lys Gly Arg Phe Thr Ile Ser Lys Thr Ala Thr Thr Val
                85                  90                  95

Asp Leu Lys Ile Thr Ser Leu Thr Thr Glu Asp Thr Ala Thr Tyr Phe
            100                 105                 110

Cys Val Ala Gly Thr Gly Leu Trp Gly Gln Gly Thr Leu Val Thr Val
        115                 120                 125

Ser Ser
    130

<210> SEQ ID NO 24
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Ala Val Gly Ser Thr Val Thr Ile Asn Cys Gln Ala Ser
            35                  40                  45

Gln Ser Val Tyr Asn Lys Asn Arg Leu Ser Trp Tyr Gln Gln Lys Pro
        50                  55                  60

Gly Gln Pro Pro Lys Arg Leu Ile Tyr Ser Ser Ser Thr Leu Asp Ser
65                  70                  75                  80

Gly Val Pro Leu Arg Phe Ser Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Leu Gly Ser Tyr Asp Cys Ser Ser Ala Asp Cys Asn Ala Phe Gly Gly
            115                 120                 125

Gly Thr Glu Val Val Val Lys
        130                 135
```

<210> SEQ ID NO 25
<211> LENGTH: 137
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Gln Pro
            20                  25                  30

Gly Ala Ser Leu Thr Leu Thr Cys Thr Ala Ser Gly Phe Thr Leu Thr
            35                  40                  45

Thr Tyr Trp Ile Cys Trp Val Arg Gln Ala Pro Gly Lys Gly Leu Glu
        50                  55                  60

Trp Val Ala Cys Ile Leu Thr Gly Ser Gly Ser Thr Tyr Tyr Ala Ser
65                  70                  75                  80

Trp Val Asn Gly Arg Phe Thr Ile Ser Lys Thr Ser Ser Thr Thr Val
                85                  90                  95

Thr Leu Gln Met Thr Ser Leu Thr Ala Ala Asp Thr Ala Thr Tyr Phe
            100                 105                 110

Cys Ala Arg Tyr Gly Gly Asp Ala Thr Tyr Asn Glu Asn Leu Trp Gly
            115                 120                 125

Gln Gly Thr Leu Val Thr Val Ser Ser
        130                 135
```

<210> SEQ ID NO 26
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Met Asp Thr Arg Ala Pro Thr Gln Leu Leu Gly Leu Leu Leu Leu Trp
1               5                   10                  15
```

```
Leu Pro Gly Ala Thr Phe Ala Gln Val Leu Thr Gln Thr Pro Ser Ser
                20                  25                  30

Val Ser Ala Ala Val Gly Gly Thr Val Thr Ile Asn Cys Gln Ala Ser
            35                  40                  45

Gln Ser Val Tyr Asn Asn Arg Leu Ser Trp Tyr Gln Gln Lys Pro
        50                  55                  60

Gly Gln Pro Pro Lys Arg Leu Ile Tyr Gly Val Ser Thr Leu Tyr Tyr
65                  70                  75                  80

Gly Val Ser Ser Arg Phe Lys Gly Ser Gly Ser Gly Thr Gln Phe Thr
                85                  90                  95

Leu Thr Ile Ser Gly Met Gln Cys Asp Asp Ala Ala Ile Tyr Tyr Cys
            100                 105                 110

Leu Gly Gly Tyr Asp Cys Ala Ser Ala Asp Cys Tyr Ala Phe Gly Gly
                115                 120                 125

Gly Thr Glu Val Val Val Lys
        130                 135
```

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Thr Pro Leu Thr Leu Thr Cys Thr Val Ser Gly Ile Asp Leu Ser
            35                  40                  45

Ser Asn Ala Met Asn Trp Val Arg Gln Ala Pro Gly Lys Gly Leu Glu
        50                  55                  60

Trp Ile Gly Ile Ile Gly Phe Ser Gly Ser Thr Asn Tyr Ala Ser Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Gly Gly Leu Asn Ile Gly Met Asn Leu Trp Gly Gln Gly Thr Leu
                115                 120                 125
```

```
Val Thr Val Ser Ser
    130

<210> SEQ ID NO 31
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Pro Ile Ser Cys Gln Ser Ser
        35                  40                  45

Gln Ser Val Tyr Asp Asn Asn Trp Leu Ala Trp Tyr Gln Gln Lys Pro
    50                  55                  60

Gly Gln Pro Pro Lys Leu Leu Val Tyr Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Asn Asp Leu Glu Cys Asp Ala Ala Thr Tyr Tyr Cys
            100                 105                 110

Ala Gly Gly Tyr Gly Asp Thr Asn Gly Gly Ala Ser Ser Phe Gly Gly
            115                 120                 125

Gly Thr Glu Val Val Val Lys
        130                 135

<210> SEQ ID NO 32
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Glu Thr Gly Leu Arg Trp Leu Leu Leu Gly Ala Val Leu Lys Gly
1               5                   10                  15

Val Gln Cys Gln Glu Gln Leu Lys Glu Ser Gly Gly Gly Leu Val Thr
            20                  25                  30

Pro Gly Gly Thr Leu Thr Leu Thr Cys Thr Val Ser Gly Phe Ser Leu
        35                  40                  45

Ser Ser Tyr Ala Met Ser Trp Val Arg Gln Ala Pro Gly Lys Gly Leu
    50                  55                  60

Glu Trp Ile Gly Ile Ile Ile Ser Gly Gly Ser Ala Tyr Tyr Ala Thr
65                  70                  75                  80

Trp Ala Lys Gly Arg Phe Thr Ile Ser Lys Thr Ser Thr Thr Val Asp
                85                  90                  95

Leu Ser Ile Thr Ser Pro Thr Thr Glu Asp Thr Ala Thr Tyr Phe Cys
            100                 105                 110

Ala Arg Ala Lys Ser Gly Thr Tyr Thr Gly Asp Tyr Phe Thr Leu Trp
            115                 120                 125

Gly Gln Gly Thr Leu Val Thr Val Ser Ser
        130                 135
```

```
<210> SEQ ID NO 33
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Asp Thr Arg Ala Pro Thr Gln Leu Leu Gly Leu Leu Leu Leu Trp
1               5                   10                  15

Leu Pro Gly Ala Arg Cys Ala Phe Glu Leu Thr Gln Thr Pro Ala Ser
            20                  25                  30

Val Glu Ala Ala Val Gly Gly Thr Val Thr Ile Lys Cys Gln Ala Ser
        35                  40                  45

Glu Ser Ile Gly Asn Ala Leu Ala Trp Tyr Gln Gln Lys Pro Gly Gln
    50                  55                  60

Pro Pro Lys Leu Leu Ile Tyr Arg Ala Ser Thr Leu Glu Ser Gly Val
65                  70                  75                  80

Pro Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Ser
            100                 105                 110

Tyr Val Gly Ser Arg Ser Thr Gly Tyr Asn Val Phe Gly Gly Gly Thr
        115                 120                 125

Glu Val Val Val Lys
    130

<210> SEQ ID NO 34
<211> LENGTH: 672
<212> TYPE: PRT
<213> ORGANISM: Homo sapiens

<400> SEQUENCE: 34

Met Ala Asp Val Phe Pro Gly Asn Asp Ser Thr Ala Ser Gln Asp Val
1               5                   10                  15

Ala Asn Arg Phe Ala Arg Lys Gly Ala Leu Arg Gln Lys Asn Val His
            20                  25                  30

Glu Val Lys Asp His Lys Phe Ile Ala Arg Phe Phe Lys Gln Pro Thr
        35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Asp Thr Asp
                85                  90                  95

Asp Pro Arg Ser Lys His Lys Phe Lys Ile His Thr Tyr Gly Ser Pro
            100                 105                 110

Thr Phe Cys Asp His Cys Gly Ser Leu Leu Tyr Gly Leu Ile His Gln
        115                 120                 125

Gly Met Lys Cys Asp Thr Cys Asp Met Asn Val His Lys Gln Cys Val
    130                 135                 140

Ile Asn Val Pro Ser Leu Cys Gly Met Asp His Thr Glu Lys Arg Gly
145                 150                 155                 160

Arg Ile Tyr Leu Lys Ala Glu Val Ala Asp Glu Lys Leu His Val Thr
                165                 170                 175
```

Val Arg Asp Ala Lys Asn Leu Ile Pro Met Asp Pro Asn Gly Leu Ser
            180                 185                 190

Asp Pro Tyr Val Lys Leu Lys Leu Ile Pro Asp Pro Lys Asn Glu Ser
        195                 200                 205

Lys Gln Lys Thr Lys Thr Ile Arg Ser Thr Leu Asn Pro Gln Trp Asn
    210                 215                 220

Glu Ser Phe Thr Phe Lys Leu Lys Pro Ser Asp Lys Asp Arg Arg Leu
225                 230                 235                 240

Ser Val Glu Ile Trp Asp Trp Asp Arg Thr Thr Arg Asn Asp Phe Met
                245                 250                 255

Gly Ser Leu Ser Phe Gly Val Ser Glu Leu Met Lys Met Pro Ala Ser
            260                 265                 270

Gly Trp Tyr Lys Leu Leu Asn Gln Glu Glu Gly Glu Tyr Tyr Asn Val
        275                 280                 285

Pro Ile Pro Glu Gly Asp Glu Glu Gly Asn Met Glu Leu Arg Gln Lys
    290                 295                 300

Phe Glu Lys Ala Lys Leu Gly Pro Ala Gly Asn Lys Val Ile Ser Pro
305                 310                 315                 320

Ser Glu Asp Arg Lys Gln Pro Ser Asn Asn Leu Asp Arg Val Lys Leu
                325                 330                 335

Thr Asp Phe Asn Phe Leu Met Val Leu Gly Lys Gly Ser Phe Gly Lys
            340                 345                 350

Val Met Leu Ala Asp Arg Lys Gly Thr Glu Glu Leu Tyr Ala Ile Lys
        355                 360                 365

Ile Leu Lys Lys Asp Val Val Ile Gln Asp Asp Asp Val Glu Cys Thr
    370                 375                 380

Met Val Glu Lys Arg Val Leu Ala Leu Leu Asp Lys Pro Pro Phe Leu
385                 390                 395                 400

Thr Gln Leu His Ser Cys Phe Gln Thr Val Asp Arg Leu Tyr Phe Val
                405                 410                 415

Met Glu Tyr Val Asn Gly Gly Asp Leu Met Tyr His Ile Gln Gln Val
            420                 425                 430

Gly Lys Phe Lys Glu Pro Gln Ala Val Phe Tyr Ala Ala Glu Ile Ser
        435                 440                 445

Ile Gly Leu Phe Phe Leu His Lys Arg Gly Ile Ile Tyr Arg Asp Leu
    450                 455                 460

Lys Leu Asp Asn Val Met Leu Asp Ser Glu Gly His Ile Lys Ile Ala
465                 470                 475                 480

Asp Phe Gly Met Cys Lys Glu His Met Met Asp Gly Val Thr Thr Arg
                485                 490                 495

Thr Phe Cys Gly Thr Pro Asp Tyr Ile Ala Pro Glu Ile Ile Ala Tyr
            500                 505                 510

Gln Pro Tyr Gly Lys Ser Val Asp Trp Trp Ala Tyr Gly Val Leu Leu
        515                 520                 525

Tyr Glu Met Leu Ala Gly Gln Pro Pro Phe Asp Gly Glu Asp Glu Asp
    530                 535                 540

Glu Leu Phe Gln Ser Ile Met Glu His Asn Val Ser Tyr Pro Lys Ser
545                 550                 555                 560

Leu Ser Lys Glu Ala Val Ser Val Cys Lys Gly Leu Met Thr Lys His
                565                 570                 575

Pro Ala Lys Arg Leu Gly Cys Gly Pro Glu Gly Glu Arg Asp Val Arg
            580                 585                 590

```
Glu His Ala Phe Phe Arg Arg Ile Asp Trp Glu Lys Leu Glu Asn Arg
            595                 600                 605

Glu Ile Gln Pro Pro Phe Lys Pro Lys Val Cys Gly Lys Gly Ala Glu
        610                 615                 620

Asn Phe Asp Lys Phe Phe Thr Arg Gly Gln Pro Val Leu Thr Pro Pro
625                 630                 635                 640

Asp Gln Leu Val Ile Ala Asn Ile Asp Gln Ser Asp Phe Glu Gly Phe
                645                 650                 655

Ser Tyr Val Asn Pro Gln Phe Val His Pro Ile Leu Gln Ser Ala Val
            660                 665                 670

<210> SEQ ID NO 35
<211> LENGTH: 10
<212> TYPE: PRT
<213> ORGANISM: Homo sapiens

<400> SEQUENCE: 35

Leu Gly Gly Arg Gly Pro Gly Gly Arg Pro
1               5                   10

<210> SEQ ID NO 36
<211> LENGTH: 25
<212> TYPE: PRT
<213> ORGANISM: Homo sapiens

<400> SEQUENCE: 36

Phe Thr Tyr Val Asn Pro Asp Phe Val His Pro Asp Ala Arg Ser Pro
1               5                   10                  15

Thr Ser Pro Val Pro Val Pro Val Met
            20                  25

<210> SEQ ID NO 37
<211> LENGTH: 13
<212> TYPE: PRT
<213> ORGANISM: Homo sapiens

<400> SEQUENCE: 37

Asn Tyr Pro Leu Glu Leu Tyr Glu Arg Val Arg Met Gly
1               5                   10

<210> SEQ ID NO 38
<211> LENGTH: 303
<212> TYPE: PRT
<213> ORGANISM: Homo sapiens

<400> SEQUENCE: 38

Cys Thr Leu Val Glu Lys Arg Val Leu Ala Leu Gly Gly Arg Gly Pro
1               5                   10                  15

Gly Gly Arg Pro His Phe Leu Thr Gln Leu His Ser Thr Phe Gln Thr
            20                  25                  30

Pro Asp Arg Leu Tyr Phe Val Met Glu Tyr Val Thr Gly Gly Asp Leu
        35                  40                  45

Met Tyr His Ile Gln Gln Leu Gly Lys Phe Lys Glu Pro His Ala Ala
    50                  55                  60

Phe Tyr Ala Ala Glu Ile Ala Ile Gly Leu Phe Phe Leu His Asn Gln
65                  70                  75                  80

Gly Ile Ile Tyr Arg Asp Leu Lys Leu Asp Asn Val Met Leu Asp Ala
                85                  90                  95

Glu Gly His Ile Lys Ile Thr Asp Phe Gly Met Cys Lys Glu Asn Val
            100                 105                 110
```

```
Phe Pro Gly Thr Thr Thr Arg Thr Phe Cys Gly Thr Pro Asp Tyr Ile
        115                 120                 125
Ala Pro Glu Ile Ile Ala Tyr Gln Pro Tyr Gly Lys Ser Val Asp Trp
    130                 135                 140
Trp Ser Phe Gly Val Leu Leu Tyr Glu Met Leu Ala Gly Gln Pro Pro
145                 150                 155                 160
Phe Asp Gly Glu Asp Glu Glu Leu Phe Gln Ala Ile Met Glu Gln
                165                 170                 175
Thr Val Thr Tyr Pro Lys Ser Leu Ser Arg Glu Ala Val Ala Ile Cys
            180                 185                 190
Lys Gly Phe Leu Thr Lys His Pro Gly Lys Arg Leu Gly Ser Gly Pro
        195                 200                 205
Asp Gly Glu Pro Thr Ile Arg Ala His Gly Phe Phe Arg Trp Ile Asp
    210                 215                 220
Trp Glu Arg Leu Glu Arg Leu Glu Ile Pro Pro Pro Phe Arg Pro Arg
225                 230                 235                 240
Pro Cys Gly Arg Ser Gly Glu Asn Phe Asp Lys Phe Phe Thr Arg Ala
            245                 250                 255
Ala Pro Ala Leu Thr Pro Pro Asp Arg Leu Val Leu Ala Ser Ile Asp
            260                 265                 270
Gln Ala Asp Phe Gln Gly Phe Thr Tyr Val Asn Pro Asp Phe Val His
        275                 280                 285
Pro Asp Ala Arg Ser Pro Thr Ser Pro Val Pro Val Pro Val Met
    290                 295                 300
```

IN VITRO METHOD FOR DIAGNOSING CENTRAL NERVOUS SYSTEM INJURY

RELATED APPLICATIONS

This application is a continuation application of PCT application PCT/US21/16740 designating the United States and filed Feb. 5, 2021; which claims the benefit of U.S. Provisional Application No. 62/970,769 and filed Feb. 6, 2020 each of which are hereby incorporated by reference in their entireties.

FIELD OF THE INVENTION

The present invention is directed to an improved in vitro method for rapidly diagnosing the occurrence and severity of a traumatic ischemic event involving the central nervous system such as a traumatic brain injury or Stroke. The method includes the use of monoclonal antibodies to detect the presence of the gamma isoform of protein kinase C (PKCγ) and PKCγ proteolytic fragments that enter the bloodstream as a result of breakdown of the blood brain barrier following an injury to the central nervous system.

SEQUENCE LISTING

The instant application contains a Sequence Listing which has been submitted electronically in ASCII format and is hereby incorporated by reference in its entirety. Said ASCII copy, created on Oct. 14, 2021, with the file name of PCT Sequence Listing.txt and is 31.6 kilobytes in size.

BACKGROUND OF THE INVENTION

Traumatic brain injury (TBI) is one of the leading causes of death in the world and is a major cause of adult disability (Langlois et al., *J. Head Trauma Rehabil.*, 21(5): 375-378 (2006)). The incidence of TBI in the US is comparable to stroke but affects younger people so it results in a greater health care burden. Approximately 5 million new cases of TBI occur in the United States every year, with an estimated annual cost of $60 billion (Yu et al., *Brain Res.*, 1287: 157-163 (2009)); Mammis et al., *Surg. Neurol.*, 71:(5), 527-531 (2009)).

Damage from traumatic brain injury (TBI) results in hyperexcitability of nerve cells, also referred to as "excitotoxicity", through both electrical and neurotransmitter activity mediated predominantly by glutamate receptors (Barr et al., *Brain Inj.*, 26: 58-66 (2012)). TBI is also an ischemic disease. Using positron emission tomography Veenith et al. reported that ischemic brain volume and hypoxic brain volume are higher after TBI than in control patients (Veenith et al., *JAMA Neurol.*, 73(5): 542-550 (2016)). Ischemia and hypoxia occur from TBI in nonoverlapping regions and a widespread reduction in oxidative metabolism is seen in most cases of TBI (Vespa, P. M., *JAMA Neurol.*, 73(5): 504-505 (2016)).

A "stroke" is clinically defined as a rapidly developing syndrome of vascular origin with focal loss of cerebral function. A stroke occurs when the blood supply to a part of the brain is suddenly interrupted (ischemic stroke) or when a blood vessel in the brain ruptures, spilling blood into the spaces surrounding the brain cells (hemorrhagic stroke). A person has a stroke every forty seconds in the U.S. Eighty-five percent of them roughly—750,000 cases per year—are ischemic, the result of a blockage within a blood vessel supplying blood to the brain. The remaining 15 percent of strokes occur when a CNS blood vessel tears and blood accumulates in the brain (Stanford Stroke Center).

Prompt diagnosis of a traumatic brain injury or stroke is critical to the victim's recovery. Delays in diagnosis and medical intervention may contribute to clinical deterioration and disability. An early diagnosis enables doctors to more effectively choose appropriate emergency interventions. A delay in assessing an accurate and certain diagnosis wastes the limited amount of time available in which the brain can respond to reperfusion and significantly increases the risk of hemorrhage after most of the permanent injury has occurred (Marler, J. R., *Ann. Emerg. Med.*, 33: 450-451 (1999)). The DEFUSE 3 trial for ischemic stroke (NIH sanctioned trial) established a 6-24 hour time window after the patient was last known to be "well" for endovascular treatment. The thrombectomy window is 6-16 hours (Albers et al., *N. Engl. J. Med.*, 378: 708-718 (2018)). Two electrophysiology studies demonstrated a significant injury effect at 8 days after suffering a sports-related concussion, with recovery by day 45, although the athlete's clinical symptoms apparently recovered between 5 and 8 days. This finding indicates that physiological perturbations persist well after apparent "clinical recovery" (McCrea et al., *J. Head Trauma Rehabil.*, 25: 283-292 (2010); Barr et al., *Brain Inj.*, 26: 58-66 (2012)). A patient taken to an emergency room with a mild traumatic head injury is given basic neurologic tests and may have neuroimaging such as MRI or CT scan. Depending on the severity of brain injury, certain drugs such as diuretics, anti-seizure drugs, and/or coma-inducing drugs may be administered. Surgery may be needed to minimize damage to brain tissues following edema and ischemia (Herring et al., *Med. Sci. Sports Exerc.*, 38(2): 395-399 (2006)).

Glutamate Release from Brain to Blood

The brain is especially vulnerable to ischemia and massive depolarization (electrical activity) of nerves following a TBI. Under those conditions, signals normally responsible for processing information are largely disrupted. Glutamate (Glu) is released in large amounts, initially from the nerve terminals and eventually by reverse transport involving astrocytes. (Szatkowski et al., *Trends Neurosci.*, 17(9):359-365 (1994); Rossi et al., *Nature*, 403: 316-321 (2000); Phillis et al., *Brain Res.*, 868(1): 105-112 (2000)). Astrocytes possess glutamate-sensitive ion channels that respond to glutamate with a prompt elevation of cytoplasmic free $Ca^{2+}$ (Cornell-Bell et al., *Science*, 247(4941): 470-473 (1990)). Astrocytes play an important role in regulating the Blood Brain Barrier.

The brain interstitial space, or "extracellular space" as it is called, is a narrow space among neural cells and capillaries. Direct measurement of glutamate in interstitial space requires microsurgical insertion of a microdialysis cannula into the brain (Chefer et al., *Curr. Protoc. Neurosci.*, 47(1): 7.1.1-7.1.28 (2009); Baker et al., *Neurochem.*, 57(4): 1370-1379 (1991)). Microdialysis studies in humans and rodents demonstrates an immediate rise in interstitial glutamate in TBI (Guerriero et al., *Curr. Neurol. Neurosci. Rep.*, 15:27 (2015)). Interstitial rise in glutamate was recorded in humans out to 4 days post-injury, and levels were directly correlated to posttraumatic mortality (Chamoun et al., *J Neurosurg.*, 113(3): 564-570 (2010); Guerriero et al. supra). The neurotoxic effect of excitatory amino acids, namely glutamate and aspartate, in the brain has been well documented and a correlation between glutamate content in the blood and the severity of acute ischemia has been shown (Castillo et al., *Stroke*, 27: 1060-1065 (1996); Castillo et al., *Lancet*, 349: 79-83 (1997)). Cerebral damage and its association with progressing stroke are attributed to increased glutamate release, or low glutamate reuptake (Davalos et al., *Stroke,* 28: 708-710 (1997)).

Activation of PKCg

Protein kinase C gamma (PKCγ or PKCg) is persistently activated and translocated to nerve membranes following brain injury. PKCg is a highly regulated cytosolic enzyme that is contained in vesicles until elevated $Ca^{2+}$ and elevated lipid, diacyl glycerol (DAG) exposure, causes activation and translocation of PKCg to the plasma membrane (Mogami et al., *J. Biol. Chem.,* 278(11): 9896-9904 (2003)). Complete activation of PKCg requires, $Ca^{2+}$, DAG as well as phosphatidyl serine (Oancea et al., *Cell,* 95:307-318 (1998); Nishizuka, Y., *Science,* 258: 607-614 (1992); Kaibuchi et al, *J. Biol. Chem.,* 258: 6701-6704 (1983); Saido et al., *Biomed. Biochim. Acta,* 50(4-6): 485-489 (1991)). Once these conditions are met the PKCg is released into interstitial space. Glutamate excitotoxicity is directly responsible for subcellular distribution and quantitative release of PKCg (Selvatici et al., *J. Neurosci. Res.,* 71: 64-71 (2002); Domanska-Janik et al., *J. Neurochem.,* 58(4): 1432-1439 (1992); O'Reagan et al., *Neurosci. Lett.,* 185: 191-194 (1995); Lee et al., *J. Clin. Invest.,* 106(6): 723-731 (2000)). Glutamate excitotoxicity induces PKCg activation, PKCg release from neurons into interstitial space, and initiates break down of the blood brain barrier which allows PKCg entry to peripheral circulation. This is the basis for the recent PKCg biomarker assay (Cornell-Bell et al., U.S. Pat. No. 6,268,223). PKCg release increases as the injury increases (Selvatici et al., *Neurochem. Int.,* 49(8): 729-736 (2006)) and diminishes as injury subsides. This makes PKCg an ideal biomarker to gauge the degree of brain injury in CNS injury such as TBI or stroke.

Localization of PKCg

PKCg is expressed solely in the brain and spinal cord and its localization is restricted to neurons (Saito, N. and Shirai, Y., *J. Biochem.,* 132: 683-687(2002)). PKCg shows a unique neuronal distribution and intracellular localization in the brain and PKCg mRNA is solely found in the brain and spinal cord (Tanaka, C. and Saito, N., *Neurochem. Int.,* 21: 499-512 (1992); Saito, N. and Shirai, Y., supra). PKC gamma has been immunologically localized in many brain regions including hippocampus, cerebral cortex, cerebellum, hypothalamus, and retina (Huang, K.-P., and Huang, F. L., *Biochem. Biophys. Res. Commun.,* 139: 320-326 (1986); Saito, N. and Shirai, Y., supra). The C1 and C2 domains of PKCg bind DAG and $Ca^2$, respectively. The C1 domain of PKCg consists of two cysteine-rich repeats (C1A and C1B), both of which bind DAG with high affinity (Ono et al., *Proc. Natl. Acad. Sci. USA,* 86: 4868-4871 (1989). Under electron microscopy, PKCg, prior to activation, is localized in the cytoplasm of the neuron including nucleus and dendrites, dendritic spines, axon and synaptic terminals (Kose et al., *J. Neurosci.,* 8: 4262-4268 (1988)). Live imaging studies using GFP (green fluorescent protein)-tagged PKCg revealed activation and a rapid cycling of this isozyme between the cytoplasm and plasma membrane in cells upon stimulation of G-protein coupled receptors or $Ca^+$-ionophore (Sakai et al., *J. Cell Biol.,* 139: 1465-1476 (1997)). Dynamic movement of PKCg occurs in response to activation by $Ca^{2+}$ and DAG. PKCg translocation is a basic molecular mechanism of this enzyme. Once PKCg is activated by $Ca^{2+}$ and DAG, it will pass through the neuron plasma membrane into brain interstitium following second messenger responses to G-protein coupled receptors as described above (Sakai et al., supra). Cerebral ischemia induces breakdown of the blood brain barrier (BBB) allowing PKCg entry into the peripheral blood (Hawkins, B. T. and Davis, T. P., *Pharmacol. Rev.,* 57: 173-185 (2005); Yang, Y. and Rosenberg, G. A., Stroke, 42: 3323-3328 (2011)).

Blood Brain Barrier Breakdown Following Ischemia

The blood brain barrier (BBB) is formed by the endothelial cells of cerebral microvessels, providing a dynamic interface between the peripheral circulation and the central nervous system. The BBB regulates transport of molecules into and out of the central nervous system (CNS), which maintains tightly controlled chemical composition of the neuronal milieu that is required for proper neuronal functioning (Sweeney et al., *Physiol. Rev.,* 99(1): 21-78 (2019)). Under ischemic stroke conditions decreased BBB Tight Junction integrity results in increased bi-directional paracellular permeability, directly contributing to cerebral vasogenic edema, hemorrhagic transformation, and increased mortality (Sandoval, K. E. and Witt, K. A., *Neurobiol. Dis.,* 32(2): 200-219 (2008)). Enhanced BBB permeability has been reported to occur after many different types of experimental acute cerebral injury (Yang, Y. and Rosenberg, G. A., *Stroke,* 42: 3323-3328 (2011). Fluid percussion and diffuse impact-acceleration models of concussion as well as other types of cerebral insults such as hypoxia-ischemia, and radiation cerebritis in the adult rat are accompanied by increased BBB permeability. The etiologies of the loss of BBB integrity has been attributed to direct mechanical disruption, or to specific mechanisms such as inflammation or excitotoxicity (Adelson et al., *Acta Neurochir. Suppl.,* 71: 104-106 (1998)). Increased permeability of the BBB from VEGF is limited by the size of the delivered substance, suggesting smaller size improved passage through BBB (Ay et al., *Brain Res.,* 1234: 198-205 (2008); Mikitsh, J. L and Chacko, A. M. *Perspect. Mediciu. Chem.,* 6: 11-24 (2014)).

PKCg Fragments

A technical problem with prior methods using PKCg as a biomarker target for diagnosing CNS injury is that the signal for full-length PKCg in peripheral blood is variable from patient to patient, so that assays focusing on PKCg detection sometimes leads to false negative results. This is partly due to the fact that in the series of events that leads to PKCg crossing the blood brain barrier, the full-length PKCg protein is broken down into proteolytic fragments, and thus detection methods aimed at the intact protein search for a diminishing target.

The interstitial site of cerebral ischemia is an excitotoxic environment with high $Ca^{2+}$, phospholipids, and high levels of DAG from damaged neurons as well as toxic neurotransmitter levels and proteases that target PKCg. Proteolytic fragments of PKCg have been identified and characterized since the 1970s (Inoue et al., *J. Biol. Chem.,* 252: 7610-7616 (1977)). An ischemic, excitotoxic environment replete with proteolytic enzymes contributes to the formation of PKCg fragments prior to release to the peripheral circulation. We have determined that PKCg proteolytic fragments appearing in a peripheral blood sample can be an additional CNS injury biomarker.

Human PKCg has the following amino acid sequence:

```
                                          (SEQ ID NO: 1)
 1 MAGLGPGVGD  SEGGPRPLFC  RKGALRQKVV  HEVKSHKFTA
   RFFKQPTFCS  HCTDFIWGIG

61 KQGLQCQVCS  FVVHRRCHEF  VTFECPGAGK  GPQTDDPRNK
   HKFRLHSYSS  PTFCDHCGSL
```

-continued

```
121 LYGLVHQGMK CSCCEMNVHR RCVRSVPSLC GVDHTERRGR
    LQLEIRAPTA DEIHVTVGEA

181 RNLIPMDPNG LSDPYVKLKL IPDPRNLTKQ KTRTVKATLN
    PVWNETFVFN LKPGDVERRL

241 SVEVWDWDRT SRNDFMGAMS FGVSELLKAP VDGWYKLLNQ
    EEGEYYNVPV ADADNCSLLQ

301 KFEACNYPLE LYERVRMGPS SSPIPSPSPS PTDPKRCFFG
    ASPGRLHISD FSFLMVLGKG

361 SFGKVMLAER RGSDELYAIK ILKKDVIVQD DDVDCTLVEK
    RVLALGGRGP GGRPHFLTQL

421 HSTFQTPDRL YFVMEYVTGG DLMYHIQQLG KFKEPHAAFY
    AAEIAIGLFF LHNQGIIYRD

481 LKLDNVMLDA EGHIKITDFG MCKENVFPGT TTRTFCGTPD
    YIAPEITAYQ PYGKSVDWWS

541 FGVLLYEMLA GQPPFDGEDE EELFQAIMEQ TVTYPKSLSR
    EAVAICKGFL TKHPGKRLGS

601 GPDGEPTIRA HGFFRWIDWE RLERLEIPPP FRPRPCGRSG
    ENFDKFFTRA APALTPPDRL

661 VLASIDQADF QGFTYVNPDF VHPDARSPTS PVPVPVM
```

All sites of PKCg proteolysis are located in the V3 variable region, which is located just N-terminally to the C3/C4 regulatory domains. See, Kishimoto et al., *J. Biol. Chem.*, 264(7): 4088-4092 (1989). In the PKCg polypeptide sequence reproduced below, the variable domains (V1, V2, V3) are denoted with single underlining and the regulatory domains (C1, C2, C3/C4) are denoted with double underlining:

(SEQ ID NO: 1)

```
MAGLGPGVGDSEGGPRPLFCRKGALRQKVVHEVKSHKFTARFFKQPTFCSHCTDFIWGIGKQGLQCQVCSFVVHRRC

HEFVTFECPGAGKGPQTDDPRNKHKFRLHSYSSPTFCDHCGSLLYGLVHQGMKCSCCEMNVHRRCVRSVPSLCGVDH

TERRGRLQLEIRAPTADEIHVTVGEARNLIPMDPNGLSDPYVKLKLIPDPRNLTKQKTRTVKATLNPVWNETFVFNL

KPGDVERRLSVEVWDWDRTSRNDFMGAMSFGVSELLKAPVDGWYKLLNQEEGEYYNVPVADADNCSLLQKFEACNYP

LELYERVRMGPSSSPIPSPSPSPTDPKRCFFGASPGRLHISDFSFLMVLGKGSFGKVMLAERRGSDELYAIKILKKD

VIVQDDDVDCTLVEKRVLALGGRGPGGRPHFLTQLHSTFQTPDRLYFVMEYVTGGDLMYHIQQLGKFKEPHAAFYAA

EIAIGLFFLHNQGIIYRDLKLDNVMLDAEGHIKITDFGMCKENVFPGITTRTFCGTPDYIAPEIIAYQPYGKSVDWW

SFGVLLYEMLAGQPPFDGEDEEELFQAIMEQTVTYPKSLSREAVAICKGFLIKHPGKRLGSGPDGEPTIRAHGFFRW

IDWERLERLEIPPPFRPRPCGRSGENFDKFFTRAAPALTPPDRLVLASIDQADFQGFTYVNPDFVHPDARSPTSPVP

VPVM
```

There are calpain cleavage sites in the V3 domain, between $Ser_{321}$ and $Ser_{322}$ and between $Phe_{338}$ and $Phe_{339}$.

Calpain preferentially cleaves substrates at a leucine or a valine residue (P2), however this does not follow with all substrates. A second recognition site containing hydrophilic amino acids (Pro, Asp/Glu, Ser and Thr) is also involved. Calpains do not cause a general degradation of cellular proteins but rather elicit a limited cleavage of their substrates, and in many instances actually activate many cellular systems including the enzyme PKCg (Zhivotovsky et al., *Biochem. Biophys. Res. Comm.*, 230(3): 481-488 (1997)).

Fragments of PKCg have been named by their identifying molecular weight from earlier biochemical studies which identified binding domains of the PKCg molecule. The first identified PKCg fragment in the literature was the 50 kDa fragment from the PKCg catalytic domain (V3) (Inoue et al., *J. Biol. Chem.*, 252: 7610-7616 (1977)). A later study (Kishimoto et al. (1989), supra)) identified two catalytic fragments of 49 kDa and 47 kDa, and a regulatory fragment of 36 kDa was identified following Calpain digestion. The 45-50 kDa fragments from these isozymes contained the catalytic domain of the kinase, and the 33-38 kDa fragments contained the PS/phorbol ester-binding domain (Huang, K. P. and Huang, F. L. (1986) supra). Fragments of 50, 45, 38, 36, 35, and 33 kDa were reconfirmed for PKCg (Huang, K. P. and Huang, F. L., *J. Biol. Chem.*, 261: 14781-14787 (1986)). It is now established that these listed PKCg fragments are persistent products of proteolysis that are quantifiable and stable in the clinical blood samples. The present invention provides a means of using these fragments in quantitative diagnostic assays for CNS injury.

SUMMARY OF THE INVENTION

Currently, there is a need for a quick, simple, and highly reliable method for diagnosing the occurrence and severity of a traumatic brain injury or stroke allowing for rapid and effective medical intervention to minimize the short and long term effects of CNS injury. The present invention provides a novel in vitro method for diagnosing an injury to CNS neurons by detecting the presence of PKCg and PKCg proteolytic fragments in a sample of venous blood drawn from a subject suspected of suffering a central nervous system injury such as traumatic brain injury or stroke. Screening for PKCg and PKCg fragments in venous blood following an ischemic event involving the central nervous system is particularly advantageous because (1) this signaling molecule is tightly controlled by glutamate receptor activation resulting from the injury; (2) this biomarker is only found in nerve cells of the brain and spinal cord; (3) PKCg is closely controlled with no basal leak into extracellular space; and (4) breakdown of the Blood Brain Barrier resulting from glutamate excitotoxicity allows PKCg and PKCg fragments to travel through the BBB and become available for detection in a peripheral blood sample. Analysis of proteolytic fragments, such as the 49-52 kDa fragment, shows this fragment can be used as a very sensitive indicator of TBI because this fragment is seen rarely and with low signal in normal human plasma. Along with this increase in diagnosis of CNS injury using fragments of PKCg, it was found that multiplexed combinations of the antibodies described herein, 1H1 (PKC11), 5H1 (PKC13) and 7H1 (PKC14) can improve the injury diagnosis as well.

The present invention is directed to a novel in vitro method for the rapid and accurate diagnosis of injury to the central nervous system (CNS). The method includes obtaining a sample of peripheral blood from a subject suspected of having suffered injury involving the central nervous system and analyzing the sample for the presence of PKCg and PKCg fragments. PKCg and PKCg proteolytic fragments are not normally present in the bloodstream of a healthy individual but cross the blood brain barrier (BBB) and enter the bloodstream following a traumatic or ischemic event involving the central nervous system. The method is also capable of determining the severity of the injury in the subject by analyzing the levels of the PKCg and PKCg fragments present in peripheral blood.

In a preferred embodiment, the present invention is directed to a novel method for the diagnosis of a traumatic brain injury (TBI) in a subject suspected of having suffered a TBI. In another embodiment, the present invention is directed to a novel method for the diagnosis of a stroke in a subject suspected of having suffered a stroke. In a preferred embodiment, the method is performed via an in vitro assay wherein the biomarkers in a peripheral blood sample are contacted with one or more monoclonal antibodies directed against at least one epitope present on the biomarkers under conditions where the antibodies will form binding complexes with the biomarkers, which complexes can be detected by methods known in the art. According to the discoveries detailed herein, the accuracy of the diagnosis and the speed with which it can be made are improved to a surprising degree by utilization of at least one anti-PKCg antibody capable of binding to particular proteolytic fragments of PKCg that include specific and unique epitopes of the PKC gamma isoform.

According to the method of the invention, a sample of peripheral blood, e.g., venous blood, is obtained from a subject suspected of having suffered a CNS injury such as TBI or stroke, and the blood sample is analyzed for the presence of biomarkers indicative of an ischemic event in the central nervous system, specifically the gamma isoform of native protein kinase C (hereinafter, PKCγ or PKCg), and one or more unique proteolytic fragments (breakdown products) of PKCg in the sample. These PKCg biomarkers, which are not normally found in the peripheral blood of healthy individuals, are able to cross the blood brain barrier (BBB) and enter the bloodstream following a central nervous system injury. The presence of PKCg and/or the PKCg proteolytic fragments in the bloodstream is an indication that the subject has suffered a CNS injury. The data disclosed herein show the heightened accuracy of the methods claimed for diagnosing the occurrence of TBI and stroke injuries. In addition, the absolute levels (amount) of PKCg biomarkers present in the peripheral blood following a TBI or stroke give an indication of the severity of the injury where higher levels of the PKCg and/or PKCg proteolytic fragments indicate a more severe traumatic event. By "higher level" is meant, e.g., in comparison to background levels found in peripheral blood samples of normal subjects, that is, subject that have no suffered a CNS injury). In addition, as these biomarkers appear in the bloodstream almost immediately following a TBI or stroke, the present method may be employed by emergency personnel in the field or emergency room to provide a quick and accurate diagnosis immediately, or within minutes of the traumatic event.

In a preferred embodiment, the accuracy and reliability of methods for identifying individuals who have suffered a TBI or stroke is increased to over 90% or greater (that is, accurate diagnosis of >9 patients out of 10) and even to levels approaching 100% by combining the detection levels for at least two of the anti-PKCg monoclonal antibodies described herein (multiplexing). By combining the detection signals from probing samples with two or more antibodies as described herein, the reliability of the diagnosis improved to essentially 100% of samples, or complete accuracy.

In additional trials, in order to improve the accuracy and reliability of a TBI or stroke diagnosis, we discovered that combining the results from probing a blood sample from a TBI or stroke patient with the anti-PKCg monoclonal antibodies described herein provided a PKCg/PKCg proteolytic fragment 'profile' or pattern that improved the accuracy and reliability of the diagnosis. Unique antibodies recognizing PKCg fragments were identified which had high sensitivity, high specificity, and low false positive results when the anti-PKCg antibodies were contacted in a TBI or stroke plasma sample.

In addition, the novel in vitro method described herein is capable of quantitating the levels (concentrations) of full-length PKCg (63-73 kDa) and of particular PKCg proteolytic fragments described herein in the blood sample and thereby provide a reliable indicator of the severity of the injury to the CNS, as higher levels of these PKCg biomarkers are indicative of more severe injury to the central nervous system. This minimally invasive diagnostic procedure can be easily performed by ambulance or emergency room personnel and can be performed with a venous blood sample and an assay kit as described herein, which kit will include all the necessary components for a quick and reliable diagnosis.

In another embodiment, the present invention also provides novel antibodies and antigen-binding fragments thereof capable of binding human PKCg, wherein the variable domain of the antibody comprises a set of six Complementarity-determining Regions, or CDRs (i.e., CDR-H1, CDR-H2, CDR-H3, CDR-L1, CDR-L2, and CDR-L3), selected from the group of CDR sets defined below:

| CDR Set No. | CDR | CDR Amino Acid Sequence | SEQ ID NO: |
|---|---|---|---|
| 1 | CDR-H1 | GFSLNYYA | SEQ ID NO: 3 |
|   | CDR-H2 | ITSDTT | SEQ ID NO: 4 |
|   | CDR-H3 | ASGGSTTSPAL | SEQ ID NO: 5 |
|   | CDR-L1 | QSVWSKNY | SEQ ID NO: 6 |
|   | CDR-L2 | SAS | SEQ ID NO: 7 |
|   | CDR-L3 | LGSYDCRSADCWT | SEQ ID NO: 8 |
| 2 | CDR-H1 | GFSLSSYA | SEQ ID NO: 9 |
|   | CDR-H2 | IISGGSA | SEQ ID NO: 10 |
|   | CDR-H3 | ARAKSGTYTGDYFTL | SEQ ID NO: 11 |
|   | CDR-L1 | ESIGNA | SEQ ID NO: 12 |
|   | CDR-L2 | RAS | SEQ ID NO: 13 |
| 3 | CDR-L3 | QSYVGSRSTGYNV | SEQ ID NO: 14 |
|   | CDR-H1 | GFTLTTYW | SEQ ID NO: 15 |
|   | CDR-H2 | ILTGSGST | SEQ ID NO: 16 |
|   | CDR-H3 | ARYGGDATYNENL | SEQ ID NO: 17 |
|   | CDR-L1 | QSVYNNNR | SEQ ID NO: 18 |
|   | CDR-L2 | GVS | SEQ ID NO: 19 |
|   | CDR-L3 | LGGYDCASADCYA | SEQ ID NO: 20 |

In further embodiments, an anti-PKCg antibody according to the invention comprises VH (Variable Heavy chain) and VL (Variable Light chain) domains, wherein the two variable domains comprise amino acid sequences selected from the group consisting of:

| antibody VH & VL domains | Variable Domain | SEQ ID NO. | amino acid sequences 12345678901234567890-12345678901234567890 |
|---|---|---|---|
| 1H1/ 1K1 | VH | 21 | METGLRWLLLVAVLKGVQCQSVEES GGRLVTPGTPLALTCTVSGFSLNYY AMNWVRQAPVKGLEWIGVITSDTTY YASWAKGRFTISKTSTTVELQITS PTTEDTATYFCASGGSTTSPALWG QGTLVTVSS |
| | VL | 22 | MDTRAPTQLLGLLLLWLPGATFA QVLTQTPSPVSAAVGSTVTINCQ ASQSVWSKNYLSWFQQKPGQPPK QLIYSASTLASGVPSRFSGSGSG TQFTLTISDVQCDDAATYYCLGS YDCRSADCWTFGGGTEVVVK |
| 4H1/ 4K1 | VH | 23 | METGLRWLLLVAVLKGVQCQSVE ESGGRLVTPGTPLTLTCTVSGFS LSLSRNAVSWVRQAPGKGLEWTG IIFGDAKTYYASWAKGRFTISKT ATTVDLKITSLTTEDTATYFCVA GTGLWGQGTLVTVSS |
| | VL | 24 | MDTRAPTQLLGLLLLWLPGATF AQVLTQTASPVSAAVGSTVTIN CQASQSVYNKNRLSWYQQKPGQ PPKRLIYSSSTLDSGVPLRFS GSGSGTQFTLTISGVQCDDA ATYYCLGSYDCSSADCNA FGGGTEVVVK |
| 7H1/ 7K3 | VH | 25 | METGLRWLLLVAVLKGVQCQSL EESGGDLVQPGASLTLTCTAS GPTLTTYWICWVRQAPGKGLE WVACILTGSGSTYYASWVNGR FTISKTSSTTVTLQMTSLTA ADTATYFCARYGG DATYNENLWGQGTLVTVSS |
| | VL | 26 | MDTRAPTQLLGLLLLWLPGATFA QVLTQTPSSVSAAVGGTVTINCQ ASQSVYNNNRLSWYQQKPGQPPK RLIYGVSTLYYGVSSRFKGSGSG TQFTLTISGMQCDDAAIYYCLGG YDCASADCYAFGGGTEVVVK |
| 20H1/ 20K3 | VH | 30 | METGLRWLLLVAVLKGVQCQSVEE SGGRLVTPGTPLTLTCTVSGIDLS SNAMNWVRQAPGKGLEWIGIIGFS GSTNYASWAKGRFTISKTSTTVD LKITSPTTEDTATYFCARGGLNI GMNLWGQGTLVTVSS |
| | VL | 31 | MDTRAPTQLLGLLLLWLPGATFA QVLTQTPSPVSAAVGGTVPISCQ SSQSVYDNNWLAWYQQKPGQPPK LLVYYASTLASGVPSRFKGSGS GTQFTLTINDLECDDAATYYCAG GYGDTNGGASSFGGGTEVVVK |
| 5H1/ 5K1 | VH | 32 | METGLRWLLLGAVLKGVQCQEQLK ESGGGLVTPGGTLTLTCTVSGFSL SSYAMSWVRQAPGKGLEWIGIIIS GGSAYYATWAKGRFTISKTSTTVD LSITSPTTEDTATYFCARAKSGT YTGDYFTLWGQGTLVTVSS |
| | VL | 33 | MDTRAPTQLLGLLLLWLPGARCA FELTQTPASVEAAVGGTVTIKCQ ASESIGNALAWYQQKPGQPPKLL IYRASTLESGVPSRFKGSGSGTE FTLTISDLECADAATYYCQSYV GSRSTGYNVFGGGTEVVVK |

Definitions

As used herein, the term "ischemic event" refers to any potentially harmful episode resulting from temporary or permanent decrease of elimination of blood flow to tissues, particularly, with respect to the present invention, any event or physiological occurrence that interrupts blood flow to a portion of the central nervous system (CNS), especially cranial blood flow, and leads to damage of the central nervous system. Specific types of ischemic events include traumatic brain injury (TBI), stroke, or other events resulting in interrupted blood flow to the CNS.

As used herein, the term "antibody" is intended to be synonymous with "immunoglobulin". As used herein, the term "antibody" refers to the native antibody, and biologically active derivatives of the native antibody, commonly referred to as "active fragments" of an antibody, such as, for example, Fab' fragments, F(ab') a fragments, or Fv fragments, as well as single-domain antibodies and single chain (scFv) antibodies. An active fragment of an antibody retains the ability to bind the antigen recognized by the full (non-fragmented) antibody.

A composition or method described herein as "comprising" (or "comprises") one or more named elements or steps is open-ended, meaning that the named elements or steps are essential, but other elements or steps may be added within the scope of the composition or method. To avoid prolixity, it is also understood that any composition or method described as "comprising" one or more named elements or steps also describes the corresponding, more limited, composition or method "consisting essentially of" (or "consists essentially of") the same named elements or steps, meaning that the composition or method includes the named essential elements and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other element or step. In any composition or method disclosed herein, known or disclosed equivalents of any named essential element or step may be substituted for that element or step, respectively.

As used herein, the term "subject" or "patient" can be any vertebrate including, e.g., a human, non-human primate, horse, pig, rabbit, dog, sheep, goat, cow, cat, guinea pig or rodent. A "patient" refers to a mammalian subject afflicted with a disease, disorder, or injury.

As used herein, the term "unique proteolytic fragment of PKCg" means any fragment of PKCg that includes an epitope not found on other naturally occurring isoforms of protein kinase C, such as protein kinase C alpha isoform (PKCa, PKCα) or protein kinase C beta isoforms I or II (PKCb$_i$ or PKCb$_{ii}$; PKCβ$_i$ or PKCβ$_{ii}$). For example, antibodies described herein are directed to segments of PKCg that do not have corresponding segments (spans of consecutive amino acid residues) on, e.g., PKCa. See, the PKCg vs. PKCa sequence comparison, below:

```
PKCγ  MAGLGPGVGDSEGGPRPL--FCRKGALRQKVVHEVKSHKFTARFFKQPTFCSHCTDFIWGIG   60
      ||    ||   ||       | ||||||||  |||||  |||  ||||||||||||||||| |
PKCα  MADVFPG-NDSTASQDVANRFARKGALRQKNVHEVKDHKFIARFFKQPTFCSHCTDFIWGFG   61

γ61   KQGLQCQVCSFVVHRRCHEFVTFECPGAGKGPQTDDPRNKHKFRLHSYSSPTFCDHCGSL   120
```

```
                  -continued
       ||| |||||| |||| |||||||| |||| ||| ||||| |||| | | |||||||||||
α62    KQGFQCQVCCFVVHKRCHEFVTFSCPGADKGPDTDDPRSKHKFKIHTYGSPTFCDHCGSL      121

γ121   LYGLVHQGMKCSCCEMNVHRRCVRSVPSLCGVDHTERRGRLQLEIRAPTADE-IHVTVGEA    180
       |||| ||||||| | |||| || |||||| |||| ||| ||| |  |  | |
α122   LYGLIHQGMKCDTCDMNVHKQCVINVPSLCGMDHTEKRGRIYL--KAEVADEKLHVTVRDA    180

γ181   RNLIPMDPNGLSDPYVKLKLIPDPRNLTKQKTRTVKATLNPVWNETFVFNLKPGDVERRL     240
       |||||||||||||||||||||||| | |||| | |||| ||| | | ||| | |||
α181   KNLIPMDPNGLSDPYVKLKLIPDPKNESKQKTKTIRSTLNPQWNESFTFKLKPSDKDRRL     240

γ241   SVEVWDWDRTSRNDFMGAMSFGVSELLKAPVDGWYKLLNQEEGEYYNVPVADAD---NCSLLQ   300
       ||| |||||| |||||| |||||||| | | |||||||||||||||||||     |  | |
α241   SVEIWDWDRTTRNDFMGSLSFGVSELMKMPASGWYKLLNQEEGEYYNVPIPEGDEEGNMELRQ   303

γ301   KFEACNYPLELYERVRMGPSSSPIPSPSPSPTDPKRCFFGASPGRLHISDESFLMVLGKG     360
       |||          ||    |||     |           |   || ||||||||
α304   KFE---------KAKLGPAGNKVISPSEDRKQPSN-----NLDRVKLTDFNFLMVLGKG     348

γ361   SFGKVMLAERRGSDELYAIKILKKDVIVQDDDVDCTLVEKRVLALGGRGPGGRPHFLTQL     420
       |||||||| | | |||||||||||| ||| || |||||||| |     |||||
α349   SFGKVMLADRKGTEELYAIKILKKDVVIQDDDVECTMVEKRVLALLDKPP-----FLTQL     420

γ421   HSTFQTPDRLYFVMEYVTGGDLMYHIQQLGKFKEPHAAFYAAEIAIGLFFLHNQGIIYRD     480
       || ||| |||||||||||| |||||||||| |||||| || |||||||| | ||||||
α404   HSCFQTVDRLYFVMEYVNGGDLMYHIQQVGKEKEPQAVEYAAEISIGLFFLHKRGIIYRD     463

γ481   LKLDNVMLDAEGHIKITDEGMCKENVFPGTTTRTFCGTPDYIAPEIIAYQPYGKSVDWWS     540
       ||||||||| |||||| |||||| |   | ||||||||||||||||||||||||||||||
α464   LKLDNVMLDSEGHIKIADEGMCKEHMMDGVITRTFCGTPDYIAPEIIAYQPYGKSVDWWA     523

γ541   FGVLLYEMLAGQPPFDGEDEEELFQAIMEQTVTYPKSLSREAVAICKGFLTKHPGKRLGS     600
       |||||||||||||||||||| |||| |  | |||||| |||  ||| ||| |||||||
α524   YGVLLYEMLAGQPPFDGEDEDELFQSIMEHNVSYPKSLSKEAVSVCKGLMTKHPAKRLGC     583

γ601   GPDGEPTIRAHGFFRWIDWERLERLEIPPPFRPRPCGRSGENFDKFFTRAAPALTPPDRL     660
       || ||    | | ||| |||| || || ||| | || |||||||||  | |||||| |
α584   GPEGERDVREHAFFRRIDWEKLENREIQPPFKPKVCGKGAENFDKFFTRGQPVLTPPDQL     643

γ661   VLASIDQADFQGFTYVNPDFVHPDARSPTSPVPVPVM    697 (SEQ ID NO: 1)
       |  |||  || ||  ||||  ||||      |
α644   VIANIDQSDFEGFSYVNPQFVHPILQS--------AV    672 (SEQ ID NO: 34)
```

As used herein the term "unique epitope of PKCg" refers to polypeptide sequences found within the full-length sequence of PKCg that are antigenic and do not have exact cognates in the amino acid sequences of other protein kinase C isoforms such as PKCa or PKCb$_i$ or PKCb$_{ii}$. From the investigative work described herein, two examples of unique epitopes of PKCg are located at amino acids 405-414 (SEQ ID NO:35) and amino acids 673-697 (SEQ ID NO:36). A further unique epitope candidate is the polypeptide comprising amino acids 306-318 of PKCg (SEQ ID NO:37). Similar sequence alignment comparisons as set forth above with PKCg vs. PKCa were performed with the other isoforms of protein kinase C, which confirmed that the epitopes identified above were unique epitopes of PKCg. Immunogenic constructs including such unique epitopes may be used to raise antibodies specific for unique epitopes of PKCg, allowing differential staining of PKCg over other isoforms of protein kinase C. For example, to elicit antibodies according to the invention, a New Zealand White rabbit was immunized with two of these unique peptide sequences (SEQ ID NO:35 and 36). As discussed below, the antibodies raised against these unique epitopes recognize (bind to) full length PKCg as well as each of the PKCg proteolytic fragments suitable for diagnosing a central nervous system injury.

BRIEF DESCRIPTION OF THE DRAWINGS

FIG. 1 shows the significant increase in TBI signal when compared to normal plasma samples stained with antibodies having VH/VL components 1H1/1K1 (PKC11), 5H1/5K1 (PKC13), or 7H1/7K3 (PKC14). A 2-tailed, unpaired student T-Test analysis comparing Mean and SE of the mean at 95% Confidence limit was completed using GraphPad Prism 8 software.

FIG. 3 shows the increase in signal of TBI samples when PKC11 (black bars) and PKC13 (gray bars) are multiplexed.

(1H1), PKC13 (5H1), and PKC14 (7H1). A 2-tailed, unpaired student T-Test analysis comparing Mean and SE of the mean at 95% Confidence limit was completed using GraphPad Prism 8 software.

Figure 6:
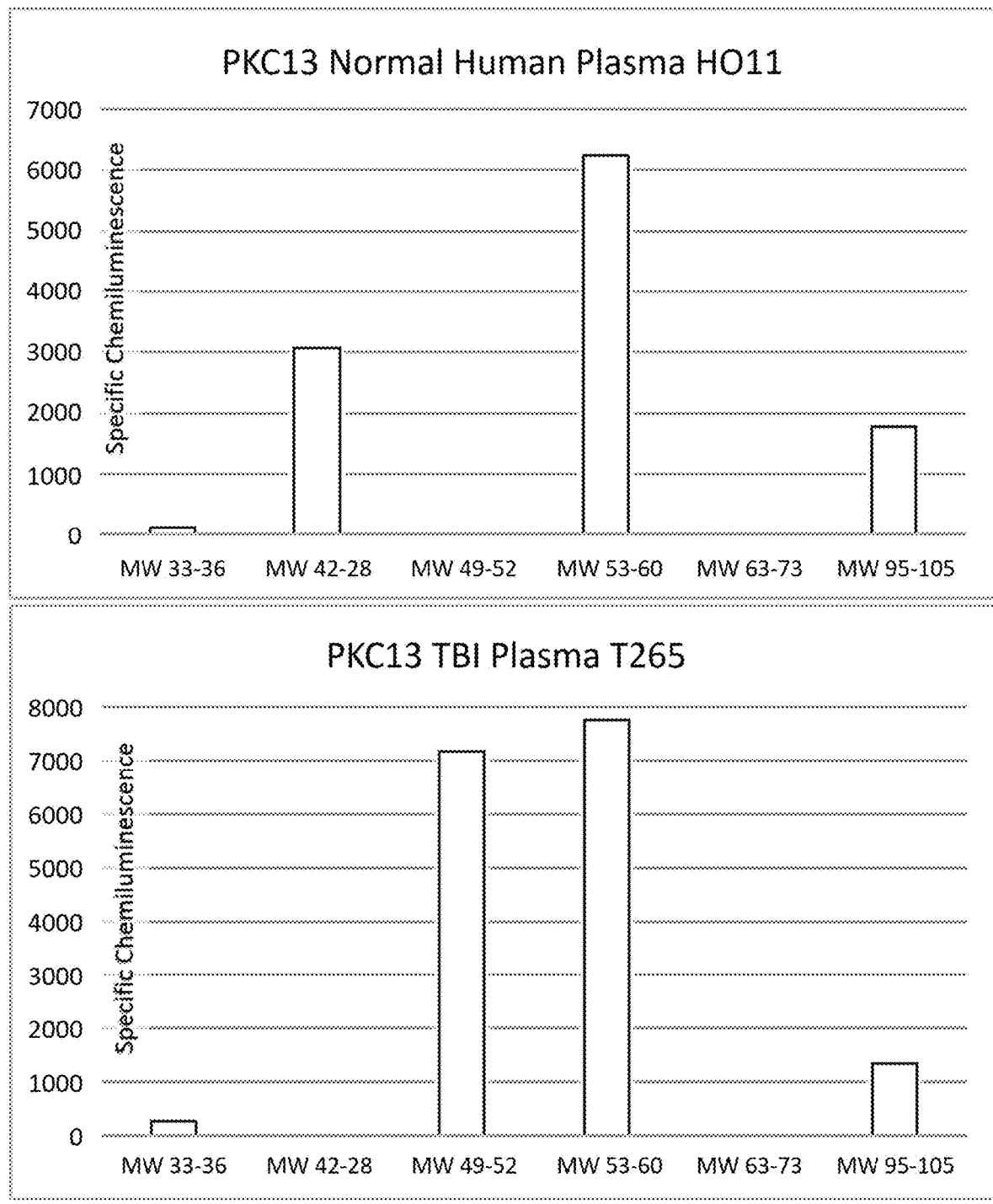

FIG. 6 shows the distribution of PKCg and the PKCg proteolytic fragments recognized by PKC13 from normal human plasma sample H011 (top graph) and TBI patient sample T265 (bottom graph).

Figures 7A, 7B, 7C:
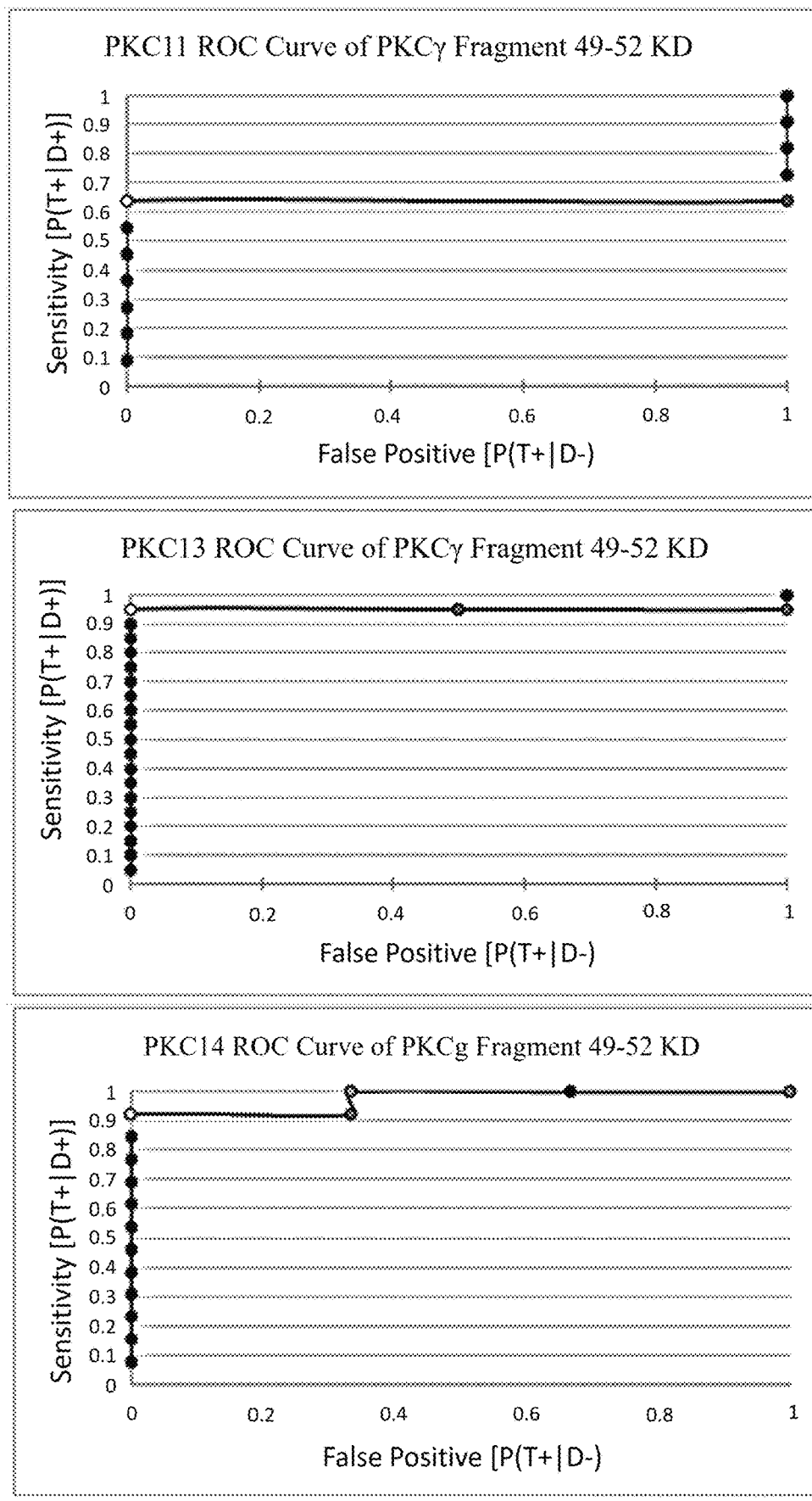

FIGS. 7A, 7B, and 7C show the ROC Curve analysis of the PKCg 49-52 kDa fragment in a TBI plasma sample stained with PKC11 (panel A), or PKC13 (panel B), or PKC14 (panel C).

Figure 8:
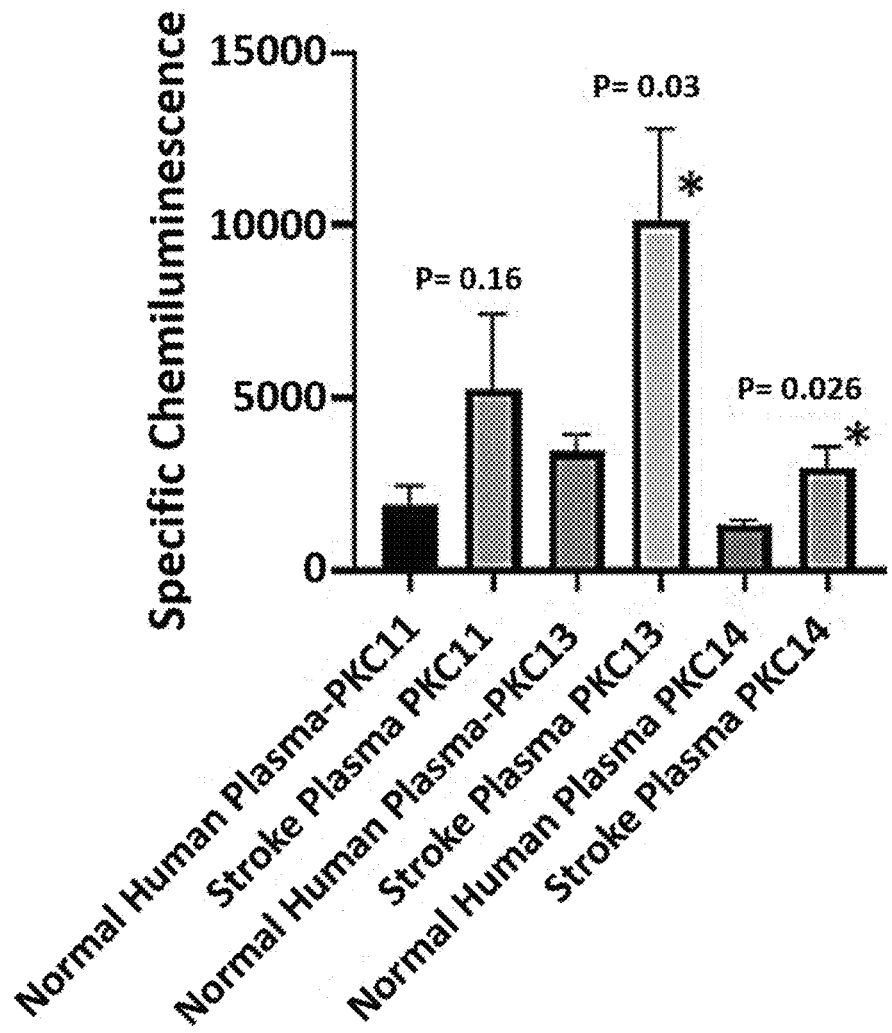

FIG. 8 shows the multiplex analysis of stroke vs. normal plasma samples stained with PKC11, PKC13, and PKC14. FIG. 8 shows the significant increase when the stroke signal is compared to normal plasma samples stained with PKC11, PKC13, or PKC14. A 2-tailed, unpaired student T-Test analysis comparing Mean and SE of the mean at 95% Confidence limit was completed using GraphPad Prism 8 software.

Figure 9A:
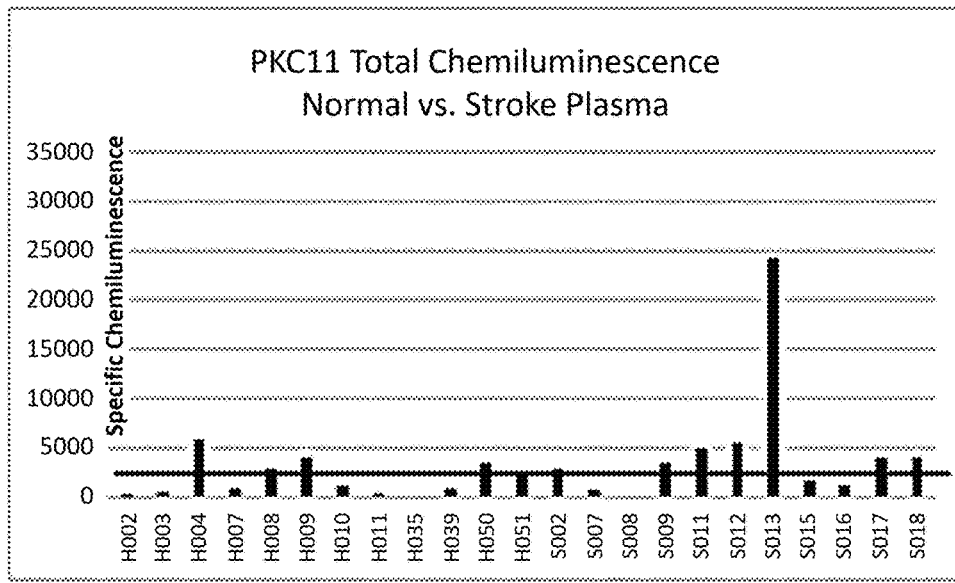
Figure 9B:
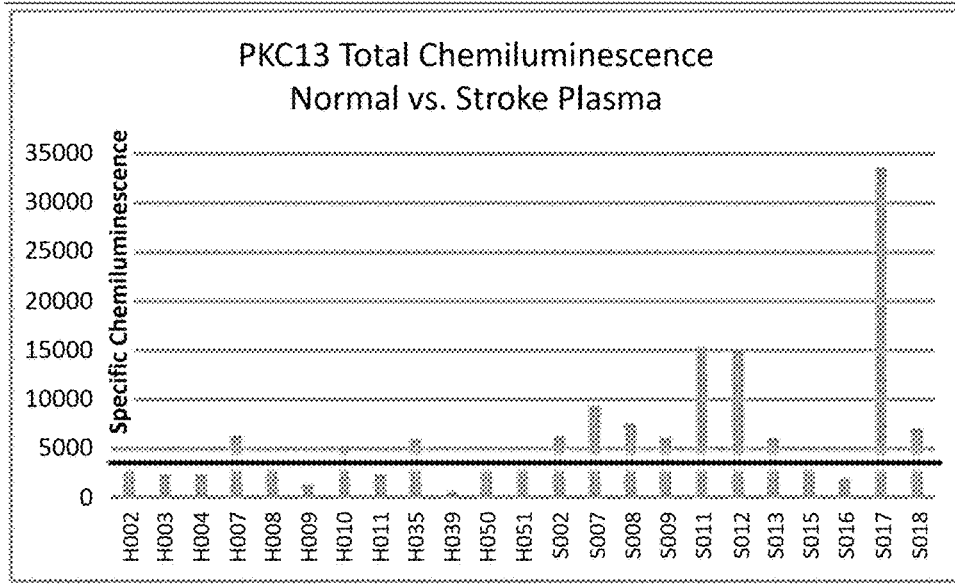
Figure 9C:
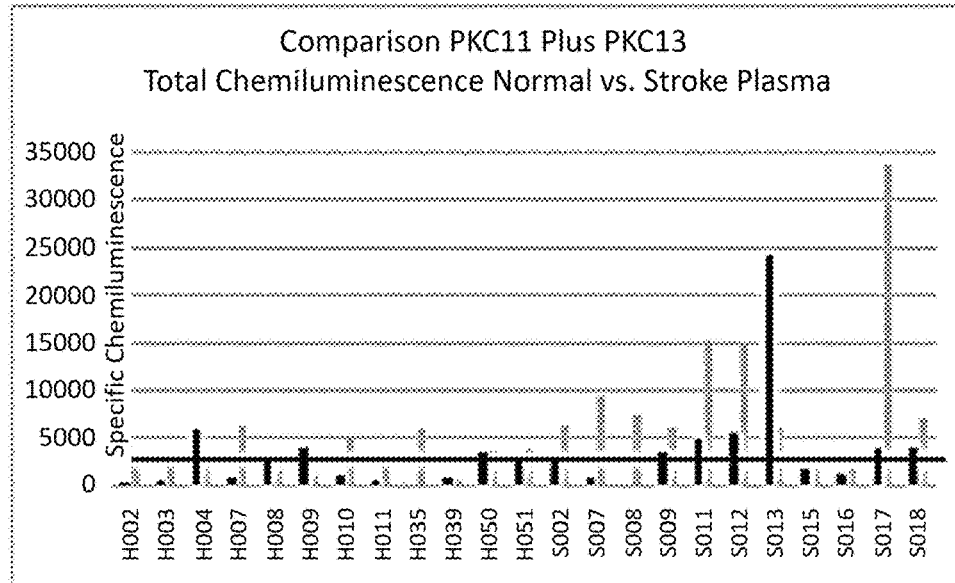

FIGS. 9A, 9B, and 9C show the levels (chemiluminescence units) of PKCg in stroke plasma samples stained with PKC11 (panel A), PKC13 (panel B), and the multiplex analysis results of stroke vs. normal plasma samples stained with both PKC11 and PKC13 (panel C).

Figures 10A, 10B, 10C:
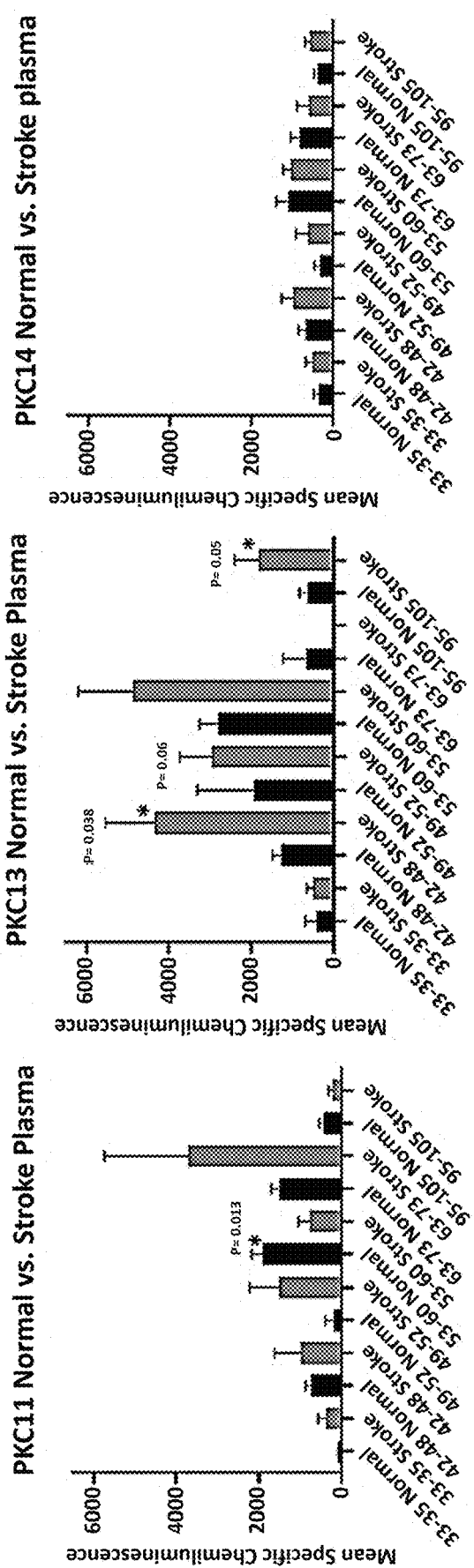

FIGS. 10A, 10B, and 10C illustrate a statistical analysis showing the levels of different PKCg proteolytic fragments in stroke vs. normal samples stained with PKC11 (panel A), PKC13 (panel B), and PKC14 (panel C). A 2-tailed, unpaired student T-Test analysis comparing Mean and SE of the mean at 95% Confidence limit was completed using GraphPad Prism 8 software.

Figure 11A:
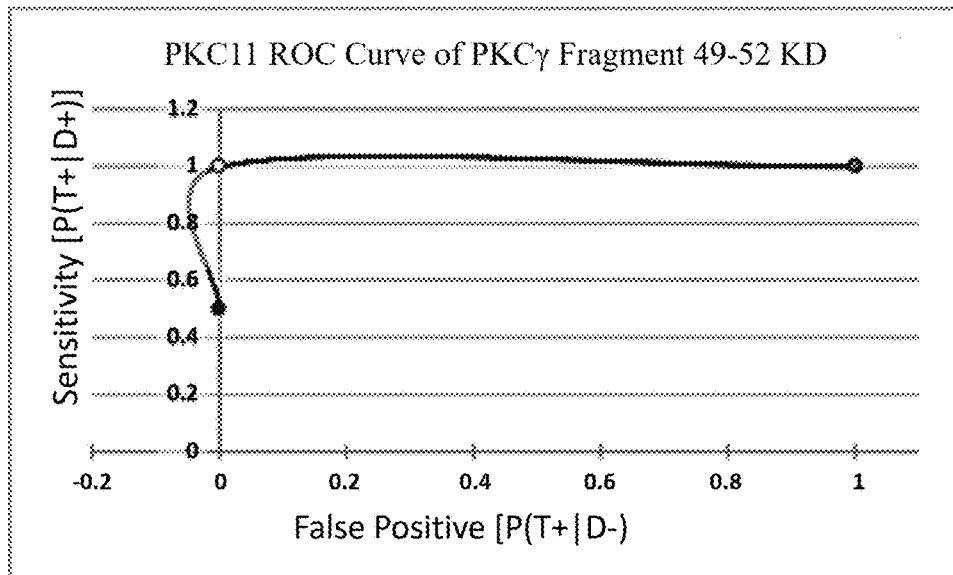
Figure 11B:
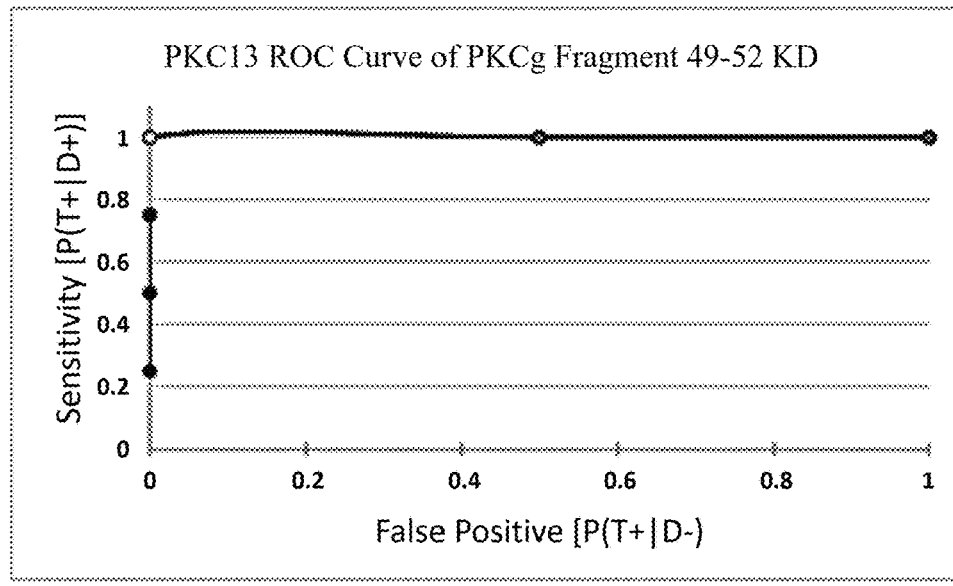
Figure 11C:
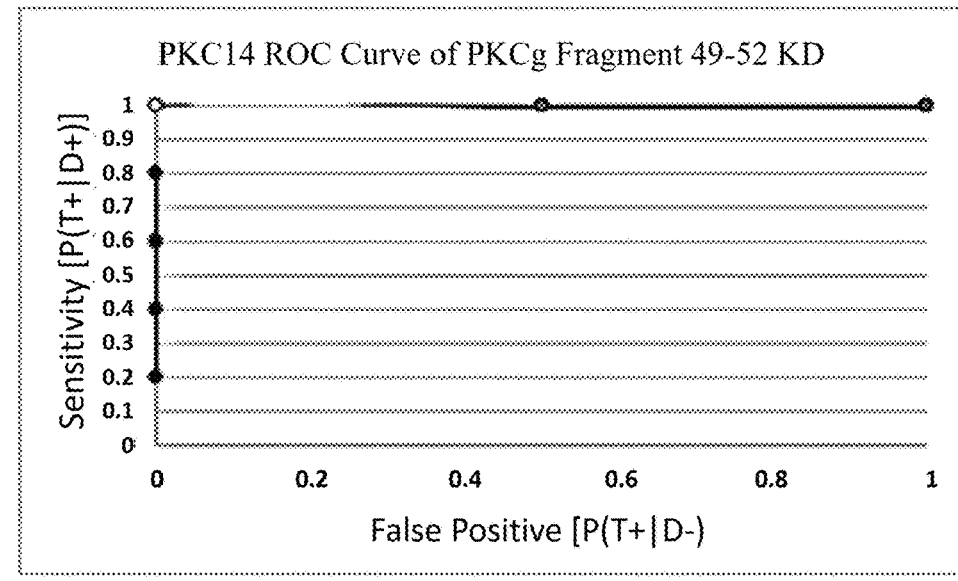

FIGS. 11A, 111B, and 11C show the ROC Curve analysis of the 49-52 kDa PKCg fragment in stroke patient samples stained with PKC11 (panel A), PKC13 (panel B), and PKC14 (panel C).

Figure 12:
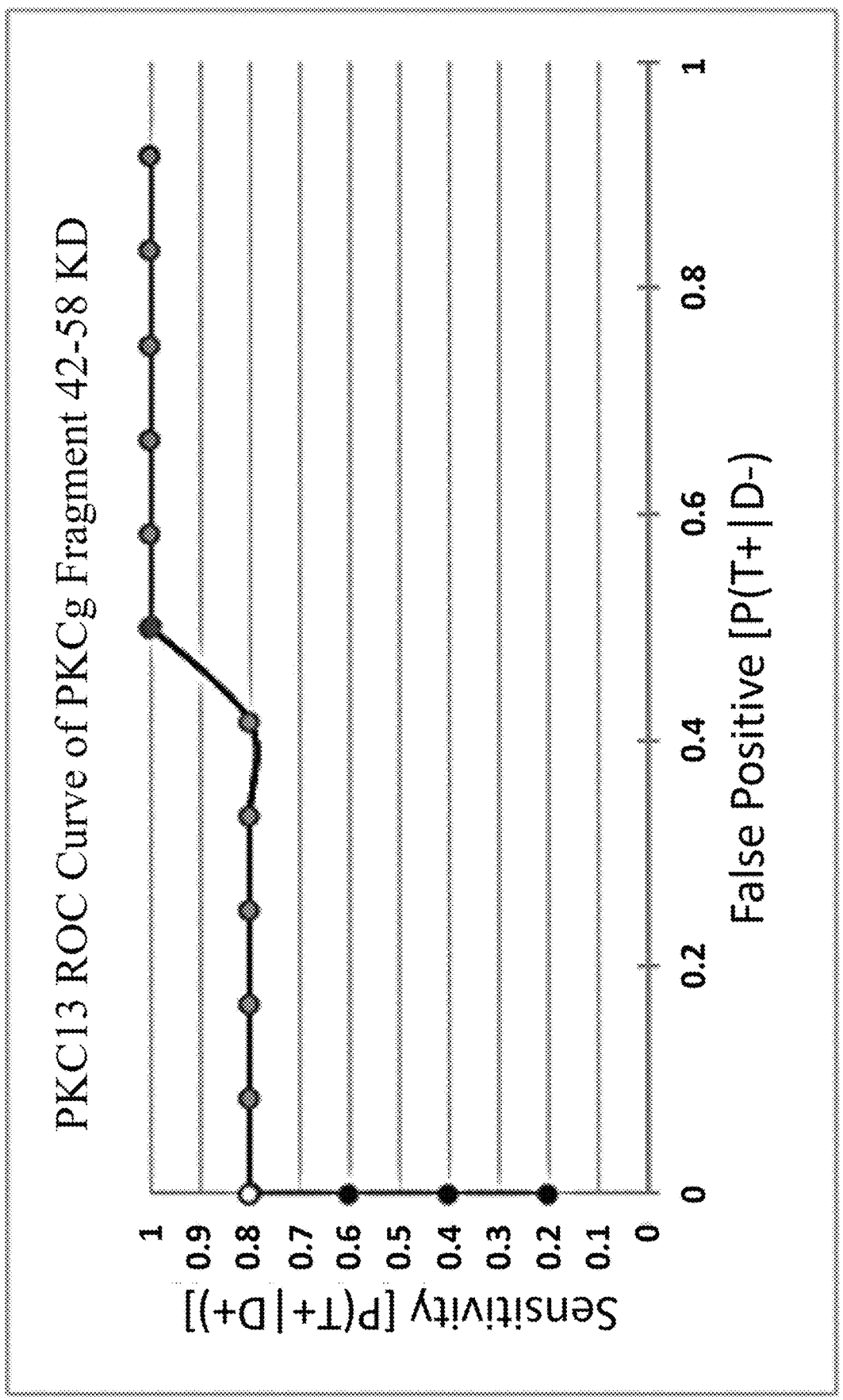

FIG. 12 shows the ROC Curve analysis of the 42-48 kDa PKCg fragment in stroke patient samples stained with PKC13.

DETAILED DESCRIPTION OF THE INVENTION

The present invention describes a rapid and accurate method for detecting damage to the central nervous system caused by a traumatic or ischemic event. In particular, the present invention is directed to a novel in vitro method for diagnosing a traumatic brain injury (TBI) or stroke. Traumatic events in the central nervous system such as TBI or stroke lead to biochemical disruptions resulting from cellular damage. These biochemical disruptions include the appearance in the bloodstream of biomarkers that are indicative of an ischemic event involving the brain, which biomarkers may be detected and quantified as reliable indicators of an ischemic episode in the central nervous system.

The diagnostic target of the method of the present invention is the gamma isozyme of protein kinase C (PKCγ or PKCg), which is confined in the central nervous system under normal conditions but which appears outside the blood brain barrier after CNS insult, such as following a TBI or stroke. In addition, the CNS interstitial excitotoxic environment resulting from CNS injury causes full-length PKCg to break down into one or more proteolytic fragments which also appear in the peripheral blood of an individual suffering CNS injury. Such peripheral PKCg and proteolytic fragments of PKCg are detectable in a blood sample once the Blood Brain Barrier loosens, providing a potential diagnostic indicator of CNS injuries including TBI and Stroke if the PKCg fragments may be preferentially detected and distinguished from other isoforms of protein kinase C. The present invention proves that such a sensitive diagnostic method is possible and provides specific materials and methods for making completely accurate determinations of CNS injury from analysis of peripheral blood in vitro from a subject suspected of having suffered a CNS insult.

Accordingly, the detection of PKCg and PKCg proteolytic fragments in a peripheral blood sample is an early diagnostic indicator of a traumatic or ischemic event involving the central nervous system, making early detection and early treatment possible. Also, advantageously, the amount of PKCg and proteolytic fragments detected in the venous blood of an individual having suffered a TBI or stroke is proportional to the degree of tissue damage, and therefore an assay for quantitating the levels of PKCg/PKCg fragments in a sample of peripheral blood as described herein is indicative of the extent of the trauma sustained in the central nervous system.

As PKCg/PKCg proteolytic fragments enter the bloodstream as the result of an ischemic event, the in vitro method of the present invention is particularly advantageous in that it provides a quick and reliable diagnosis of TBI or stroke, particularly within the critical time period where early detection and treatment of CNS damage can prevent permanent damage. As such, preferably the blood sample is drawn from the subject suspected of having suffered a traumatic brain injury or stroke immediately following the ischemic event or as soon as possible thereafter, preferably within 6 to 24 hours of the time of the CNS injury, more preferably within 6-16 hours of the time of the CNS injury.

The present method may employ any technique known in the art for detecting/quantifying the presence of a protein in a biological sample. For example, a sandwich-type assay capable of detecting the presence of PKCg and one or more PKCg proteolytic fragment(s) in a blood sample may be used. According to the method, a biological sample from a patient suspected of having suffered a CNS injury is loaded into a detection vessel that separates and immobilizes the target PKCg protein and one or more of its proteolytic fragments. The immobilized target proteins/polypeptides are then contacted with a first anti-PKCg (primary) antibody raised against a unique epitope on the PKCg protein under conditions that facilitate the formation of PKCg/primary antibody binding complex. A subsequent wash step may be employed to remove any unbound protein/antibody from the rest of the sample mixture. A secondary detectably labeled antibody, e.g., conjugated with a fluorescent tag, capable of binding to the primary antibody, is then contacted with the target/primary antibody complex and the detectable label (e.g., fluorescent signal) is detected and the amount of PKCg and/or PKCg proteolytic fragment(s) present in the sample is calculated.

Any known in vitro method in the art for detecting the presence of a protein in a sample may be employed in the present method for diagnosing TBI or stroke. Preferably, PKCg is detected in a sample of blood from a mammalian subject by contacting the sample with a binding partner for PKCg, that is, a peptide, immunoglobulin, small molecule, or other moiety capable of forming an association complex with PKCg. Most preferably, the PKCg in a sample is detected using the anti-PKCg monoclonal antibodies as described herein to form a PKCg/anti-PKCg antibody binding complex. Detection and quantitation of the PKCg/anti-PKCg antibody binding complex may also be performed by methods well known in the art including, but not limited to, gas chromatography mass spectroscopy, thin layer chromatography, hydroxyl apatite chromatography, high pressure liquid chromatography, enzyme-linked immunosorbent assay, etc. Preferably, the blood sample is analyzed via a fluorescent assay or the chemiluminescent capillary assay method described below.

In another embodiment, the present invention is directed to a point of care assay kit for diagnosing a traumatic brain injury or stroke from the blood sample of a subject suspected of sustaining such a CNS injury. The point of care assay kit will include all materials necessary for a rapid immunoassay for diagnosis of TBI or stroke according to the method of the present invention. Materials include reagents, vessels, a handheld reader with wireless connection to a computer for rapid download of patient information, instruments, and/or instructions necessary for performing the method. A point of care assay kit is particularly suitable for use by emergency medical personnel to rapidly triage a patient based on a definitive diagnosis of an ischemic event such as TBI or stroke.

Examples illustrating the diagnostic methods of the present invention are set forth below. The examples are provided to demonstrate methods and reagents useful for practicing the invention and are intended to illustrate the invention without limiting the scope of the invention. In light of the present disclosure and the general level of skill in the art, practitioners will appreciate that numerous changes, modifications, and alterations can be employed without departing from the scope of the presently disclosed subject matter.

EXAMPLES

Example 1. Production of Anti-PKCg Monoclonal Antibodies in Rabbits

Monoclonal antibodies against PKCg were generated in New Zealand White rabbits. One New Zealand White rabbit was immunized with a 303-amino acid polypeptide comprising amino acids 395-697 of PKCg:

```
                                          (SEQ ID NO:38)
CTLVEKRVLALGGRGPGGRPHFLTQLHSTFQTPDRLYFVMEYVTGGDLMYH

IQQLGKFKEPHAAFYAAEIAIGLFFLIINQGIIYRDLKLDNVMLDAEGIIK

ITDFGMCKENVFPGTTTRTFCGTPDYIAPEIIAYQPYGKSVDWWSFGVLLY

EMLAGQPPFDGEDEEELFQAIMEQTVTYPKSLSREAVAICKGFLTKHPGKR

LGSGPDGEPTIRAHGFFRWIDWERLERLEIPPPFRPRPCGRSGENFDKFFT

RAAPALTPPDRLVLASIDQADFQGFTYVNPDFVHPDARSPTSPVPVPVM.
```

A second New Zealand White rabbit was immunized with two shorter peptides having unique sequences from the C3/C4 catalytic domain of PKCg comprising amino acids 405-414 (Peptide #1) comprising the amino acid sequence: LGGRGPGGRP (SEQ ID NO:35), and amino acids 673-697 (Peptide #2) comprising the amino acid sequence:

FTYVNPDFVHPDARSPTSPVPVPVM (SEQ ID NO:36). Peptides #1 and #2 were synthesized with an N-terminal cysteine residue that was used as a reactive site to link plural peptides to a keyhole limpet hemocyanin (KLH) carrier protein.

The immunizations of both rabbits followed a standard 78-day protocol (ImmunoPrecise Antibodies, Ltd, Victoria Vancouver Canada) as follows: Day 0: control serum collection/Pre-immune Bleed; Day 1: primary injection to immunize with 0.25 mg antigen in complete Freund's Adjuvant; Day 14: Boost with 0.1 mg antigen in Incomplete Freund's Adjuvant; Day 28: Serum Collection (25 ml per rabbit); Day 42: Second Boost with 0.10 mg antigen in Incomplete Freund's Adjuvant; Day 56: second serum collection (25 ml per rabbit) and Third booster with 0.10 mg antigen in Incomplete Freund's Adjuvant; Day 72: serum collection 50 ml per rabbit; Day 78: ELISA titration to verify antibody concentration in rabbits.

Prior to injection, each peptide (antigen) was mixed 1:1 in Complete Freund's Adjuvant (CFA) for primary immunization. Subsequent booster injections (described in 78-day protocol above) were carried out in a 1:1 mixture of antigen in Incomplete Freund's Adjuvant (ICFA). The mixture of peptide and adjuvant was split into 4 equal portions and injected subcutaneously at four sites in the fore and hind quarters of each rabbit.

Test bleeds were performed on Day 28, Day 56, and Day 72 for each rabbit and serum was tested by indirect ELISA. It was determined that the titres of both rabbits were suitable for rabbit monoclonal antibody testing procedures. Both rabbits showed similar titres in indirect ELISA. Indirect ELISA uses both types of antibodies to amplify the signals for better detection. Indirect ELISA technique was performed as follows: 96-well plates were incubated with antigens and washed to block non-specific binding. Primary antibodies were added and washed. Enzyme-linked secondary antibody was added and washed. The indirect antibody is enzyme-linked to a colorimetric end point which allows quantification of antibody bound to the plate using a spectrometer.

Approximately 30 ml of heparinized whole blood was drawn on each serum collection described above from each rabbit and pooled for B cell culturing. Peripheral blood mononuclear cells (PBMCs) were isolated from the whole blood of each rabbit and the supernatants were cultured in 40×96-well plates and were screened by indirect ELISA against PKCg on day 9. Antigen-positive wells were preserved in Invitrogen RNA lysis buffer (ThermoFisher) and stored at −80° C.

cDNA was synthesized from individual RNA samples and 2 rounds of PCR performed to prepare the antibody variable region cDNA for cloning. Rabbit IgG heavy chain cDNAs and rabbit IgG kappa light chain cDNAs were cloned into mammalian expression vectors. Expression constructs were co-transfected into HEK 293 cells and cell culture supernatants assayed by sandwich ELISA. Transfected cell culture supernatants were further tested using Multi-Antigen Print ImmunoAssay, MAPIA (Lyashchenko et al., *J. Immunol. Methods*, 242(1-2): 91-100 (2000)).

Cloning of the top ranked 28 positives proceeded to Phase III cloning. 22 clones, each in 1.5 ml of transfected supernatant were further tested. Five clones were selected for 50 ml scale expression/purification (see Table 1) using Chembio Diagnostic Systems Multi-Antigen Print ImmunoAssay (MAPIA) technique where cell culture supernatants are immobilized on nitrocellulose membranes followed by antibody detection using standard chromogenic immunodevelopment.

TABLE 1

Top five clones selected and yield of 50 mL scale expression/purification

|   | Clone (HC) | Clones (κC) | Batch number | Conc. (mg/ml) | Amount (mg) |
|---|---|---|---|---|---|
| 1 | 1H1 | 1K1 | 1777 | 1.6 | 3.3 |
| 2 | 4H1 | 4K1 | 1778 | 1.7 | 0.7 |
| 3 | 7H1 | 7K3 | 1779 | 1.4 | 3.2 |
| 4 | 20H1 | 20K3 | 1780 | 1.9 | 1.4 |
| 5 | 5H1 | 5K1 | 1781 | 1.5 | 4.6 |

The DNA sequences of the five clones in Table 1 were determined.

DNA Sequence Analysis of Rabbit IgG Heavy and Light Antibody Chains

The rabbit IgG heavy chain was isolated and sequenced and is approximately 1200 bp. The rabbit kappa light chain was isolated and sequenced and is approximately 700 bp. It was determined that the heavy and light chain DNA sequences from each clone in Table 1 (1H1/1K1, 4H1/4K1, 7H1/7K3, 20H1/20K3, and 5H1/5K1) all have different sequences within the variable region. The variable region amino acid sequences for the five clones encoded by the isolated DNAs are set forth below in Table 2. The three heavy chain Complementarity Determining Regions (CDR-H1, CDR-H2, and CDR-H3) and the three light chain Complementarity Determining Regions (CDR-L1, CDR-L2, and CDR-L3) for each clone are underlined in Table 2.

TABLE 2

Variable Domain Amino Acid Sequences for Rabbit Anti-PKCγ Antibodies

| VH and VL Clones | Variable Domain | SEQ ID NO. | amino acid sequences 12345678901234567890-12345678901234567890 |
|---|---|---|---|
| 1H1 | VH | 21 | METGLRWLLLVAVLKGVQCQSVEESG GRLVTPGTPLALTCTVS<u>GFSLNYYAM NW</u>VRQAPVKGLEWIGV<u>ITSDTTYYAS WAK</u>GRFTISKTSTTVELQITSPTTED TATYFC<u>ASGGSTTSPAL</u>WGQGTLV TVSS |
| 1K1 | VL | 22 | MDTRAPTQLLGLLLLWLPGATFAQV LTQTPSPVSAAVGSTVTINC<u>QASQS VWSKNYL</u>SWFQQKPGQPPKQLIY<u>SA STL</u>ASGVPSRFSGSGSGTQFTLTIS DVQCDDAATYYC<u>LGSYDCRSADCWT</u> FGGGTEVVVK |
| 4H1 | VH | 23 | METGLRWLLLVAVLKGVQCQSVEESG GRLVTPGTPLTLTCTVS<u>GFSLSLSRNA</u> VSWVRQAPGKGLEWTGI<u>IFGDAKTYY ASW</u>AKGRFTISKTATTVDLKITSLTT EDTATYFC<u>VAGTGL</u>WGQGTLVT VSS |
| 4K1 | VL | 24 | MDTRAPTQLLGLLLLWLPGATFA QVLTQTASPVSAAVGSTVTINCQ AS<u>QSVYNKNRL</u>SWYQQKPGQPPK RLIY<u>SSS</u>TLDSGVPLRFSGSGSG TQFTLTISGVQCDDAATYY<u>CLGS YDCSSADCNA</u>FGGGTEVVVK |
| 7H1 | VH | 25 | METGLRWLLLVAVLKGVQCQSLEESGGDLV QPGASLTLTCTAS<u>GFTLTTYW</u>ICWVRQAPGK GLEWVACI<u>LTGSGSTYYASW</u>VNGRFTISKT SSTTVTLQMTSLTAADTATYFC<u>ARYGGDA TYNENL</u>WGQGTLVTVSS |
| 7K3 | VL | 26 | MDTRAPTQLLGLLLLWLPGATFAQVLTQTP SSVSAAVGGTVTINCQAS<u>QSVYNNNRL</u>SWYQ |

TABLE 2-continued

Variable Domain Amino Acid Sequences for Rabbit Anti-PKCγ Antibodies

| VH and VL Clones | Variable Domain | SEQ ID NO. | amino acid sequences 12345678901234567890-12345678901234567890 |
|---|---|---|---|
|  |  |  | QKPGQPPKRLIY<u>GVS</u>TLYYGVSSRFKGSGSG TQFTLTISGMQCDDAAIYY<u>CLGGYDCASA DCYA</u>FGGGTEVVVK |
| 20H1 | VH | 30 | METGLRWLLLLVAVLKGVQCQSVEESGGR LVTPGTPLTLTCTVS<u>GIDLSSNAMNW</u>VR QAPGKGLEWIGI<u>IGFSGSTNYASW</u>AKGRF TISKTSTTVDLKITSPTTEDTATYFC <u>ARGGLNIGMNL</u>WGQGTLVTVSS |
| 20K3 | VL | 31 | MDTRAPTQLLGLLLLWLPGATFAQVL TQTPSPVSAAVGGTVPISCQSS<u>QSVY DNNW</u>LAWYQQKPGQPPKLLVY<u>YASTL</u> ASGVPSRFKGSGSGTQFTLTINDLEC DDAATYY<u>CAGGYGDTNGGASS</u>FGGG TEVVVK |
| 5H1 | VH | 32 | METGLRWLLLGAVLKGVQCQEQLKESGG GLVTPGGTLTLTCTVS<u>GFSLSSYAM</u>SWVR QAPGKGLEWIGI<u>IISGGSAYYATW</u>AKGRF TISKTSTTVDLSITSPTTEDTATYFC <u>ARAKSGTYTGDYFTL</u>WGQGTLVTVSS |
| 5K1 | VL | 33 | MDTRAPTQLLGLLLLWLPGARCAFELT QTPASVEAAVGGTVTIKCQAS<u>ESIGNA</u> LAWYQQKPGQPPKLLIY<u>RAS</u>TLESGV PSRFKGSGSGTEFTLTISDLECADAA TYYC<u>QSYVGSRSTGYNV</u>FGGGTEVVVK |

The sequence data indicate that all the antibody clones recovered have different variable region sequences suggesting that all rabbit monoclonal antibodies recovered bind to different epitopes on the PKCg protein.

Cloning, Expression, and Purification of Five Monoclonal Antibodies

The rabbit IgG heavy chain DNA for each clone and the rabbit kappa light chain DNA for each clone were cloned separately into a CMV expression vector. Lymphocytes were fused with rabbit myeloma cells (240E-W) in the presence of polyethylene glycol. The resulting hybridoma clones were grown in tissue culture medium until mid-log growth was reached (ImmunoPrecise proprietary methods). Hybridomas were isotyped for IgG, IgM, and IgA; clones chosen expressed IgG isotype. Clones were probed against Proteintech Recombinant PRKCG (catalog ag5910) using a Multi-Antigen Print Immunoassay (MAPIA) developed by Chembio Diagnostic Systems Inc. (Lyashchenko et al., *J. Immunol. Methods,* 242(1-2): 91-100 (2000)). Anti-PKCg monoclonal antibodies made from the cloned heavy and light chains were tested for binding activity, and three high affinity anti-PKCg mAbs, designated PKC11 (1H1/1K1), PKC13 (5H1/5K1), and PKC14 (7H1/7K3), respectively, were selected for further testing.

Example 2. Analysis of Anti-PKCg Monoclonal Antibody Binding to PKCg Proteolytic Fragments in Diagnosing TBI from Human Plasma Samples The three selected rabbit monoclonal antibodies referenced above, PKC11, PKC13, and PKC14 were used to detect the presence of PKCg and PKCg proteolytic fragments in samples of blood obtained from TBI or stroke patients. The results described below demonstrate that all three rabbit monoclonal antibodies display unique staining patterns for the clinical samples from normal human plasma (control) vs. plasma from TBI or stroke patients. In order to quantitate the different fragment staining profiles for each antibody and the effects seen for normal clinical plasma samples vs. TBI samples, the composite specific chemiluminescence signal was graphed for each sample stained (complexed) with the monoclonal antibodies. A capillary electrophoresis chemiluminescence immunoassay (Raybiotech, Norcross, Ga.) was used to generate the signal levels for a cohort of 33 TBI plasma samples and 12 normal human control plasma samples.

Analysis of Antibody/PKCg Binding Data by Receiver Operator Characteristic (ROC) Curves For the present analysis of comparing the PKCg/PKCg proteolytic fragment binding profiles for the three monoclonal antibodies with the plasma of TBI and stroke patients vs. plasma from normal subjects (control), ROC curves compared the probabilities of overlap between Sensitivity and False Positive (1-Specificity) samples in the clinical cohorts described above. Sensitivity for this purpose was described as probability (P) that a positive test result overlapped with a positive disease (TBI or stroke) [P(Test+|Disease+). Similarly testing for the False Positives, we used the [P(Test+|Disease−), a condition where there is a positive test when there is no disease. An Excel pivot table application was used to count the number of healthy vs. disease samples. The Sensitivity was calculated using (=SUM individual disease samples)/total of all disease samples). False Positives were calculated using the (=SUM each individual healthy sample/total of all healthy samples). Specificity is defined as (1-False Positives). This statistical method maximizes sensitivity and identifies the probability of false positives. The cut-off point for each ROC curve between healthy and disease samples was calculated and then related to the total chemiluminescence signal that is represented by those probabilities. The cut-off for each sample cohort stained with PKC11, PKC13, and PKC14 antibodies are represented by a line in each graph below.

Analysis of Normal and TBI Samples by Chemiluminescence Capillary ELISA

All normal and TBI plasma samples were screened with each of the three anti-PKCg monoclonal antibodies for the presence of PKCg and PKCg proteolytic fragments via a chemiluminescence capillary ELISA assay. Advantageously, the chemiluminescence capillary ELISA utilizing the PKCg and PKCg fragment detection antibodies as immunoprobes according to the present disclosure, provides a highly sensitive method for detecting the presence of PKCg and/or PKCg proteolytic fragments present in a sample of venous blood of an individual following a possible traumatic brain injury or stroke.

Assaying TBI Samples

Briefly, to conduct the chemiluminescent capillary ELISA in this example, reagents and individual plasma from Normal vs. TBI clinical samples were loaded into an automated Western blot machine (using the Auto-Western service from RayBiotech Life, Inc). In the first step, sample is loaded into the capillary automatically. Proteins are then separated by size as they electrophoretically migrate through a stacking and separation matrix. The separated proteins are then immobilized on the capillary wall via a proprietary photo-activated capture chemistry. Target proteins, i.e., PKCg and/or PKCg proteolytic fragments were identified using a primary antibody, e.g., the rabbit monoclonal antibodies described herein, and immunoprobed with an HRP-conjugated secondary goat anti-rabbit IgG antibody and chemiluminescent substrate. An electropherogram is produced which plots the baseline, molecular weight and quantitative chemiluminescence signal of each peak. The quantitative signal was derived for each molecular weight band in every electropherogram. Each quantitative chemiluminescence signal was generated using the following formula; (C2-C1/C1), where C2 equals Area Under the Curve and C1 equals the baseline for that sample. This specific chemiluminescence measure was used in comparisons of all normal human plasma compared to TBI or stroke plasma samples after staining with antibodies, i.e., PKC11, PKC13, or PKC14. Statistical comparisons were made using GraphPad Prism 8 software. The resulting specific chemiluminescence signal was detected and quantitated, with sensitivity down in the picograms/ml range, providing a direct measure of TBI biomarkers, i.e., PKCg, and/or PKCg proteolytic fragments.

A total of 201 human plasma samples were analyzed using the using the automated Western blot technology. Normal Human Plasma samples were stained (contacted) with PKC11 (n=13), PKC13 (n=13), and PKC14 (n=14). A minimum of 13 individual normal human plasma samples were analyzed with each rabbit monoclonal antibody. Accounting for repeated measures from comparisons on five separate dates, a total of 56 normal human plasma samples were analyzed via the capillary ELISA assay. Plasma from TBI patients were also analyzed against (contacted with) PKC11 (n=34), PKC13 (n=33), and PKC14 (n=33). A minimum of 33 individual samples were analyzed for each rabbit monoclonal antibody and monoclonal antibody combinations. A total of 145 TBI plasma samples were run and correlated from 5 separate dates.

All statistical comparisons were run using GraphPad Prism 8 software (GraphPad Software, La Jolla, Calif.). The chemiluminescence signals from a cohort of normal vs. a cohort of TBI samples were compared. An unpaired 2-tailed Student T-test was run assuming a parametric distribution. A Welch's correction was used to test for equal SD of both samples. P Values are significant at P<0.05. Mean and Standard Error of the mean were calculated at the 95% confidence level.

Composite Signal Comparison of TBI Vs. Normal Plasma Samples Stained with Anti-PKCg mAbs PKC11, PKC13, and PKC14

A Chemiluminescent Capillary Western Blot Analysis (RayBiotech, GA) was used to characterize the PKCg signal in PKC11, PKC13, and PKC14 stained samples of normal human plasma vs. Traumatic Brain Injury plasma. Statistical comparisons were made using a 2-Tailed, unpaired Student T-Test at the 95% confidence limit. For each of the three rabbit monoclonal antibodies tested there was a significantly higher chemiluminescence signal for TBI plasma samples when compared to normal plasma samples. The results are shown in FIG. 1.

Figure 1:
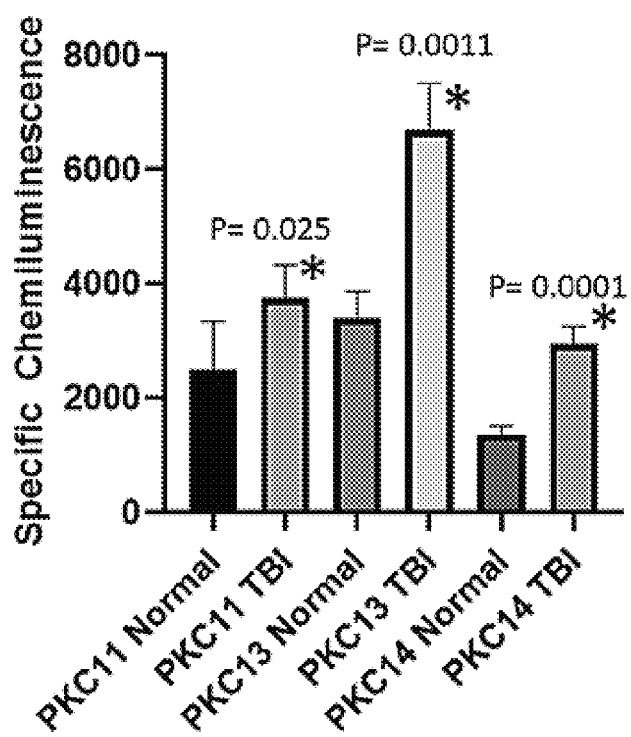
FIG. 1 shows the results of a chemiluminescent capillary ELISA used to detect binding of the anti-PKCg antibodies in peripheral the blood samples of normal (control) vs. TBI patients.

As seen in FIG. 1, the staining patterns of individual samples (normal vs. TBI) are unique with the different rabbit monoclonal antibodies PKC11, PKC13, and PKC14 and for each antibody, signals are higher in the TBI plasma samples vs. the normal plasma samples.

Figure 2A:
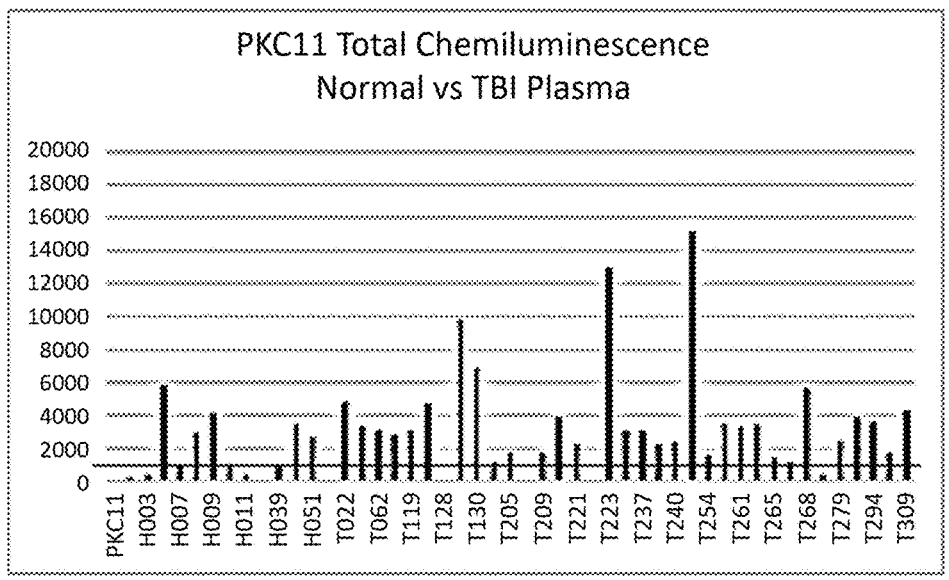
FIGS. 2A, 2B, and 2C show the levels (chemiluminescence units) of PKCg in plasma samples stained with the anti-PKCg antibodies PKC11 (panel A), PKC13 (panel B), and PKC14 (panel C), in normal (control) subjects vs. TBI plasma samples. Levels of PKCg/PKCg fragments show an increase in the plasma of TBI patients compared with normal controls.
Figure 2B:
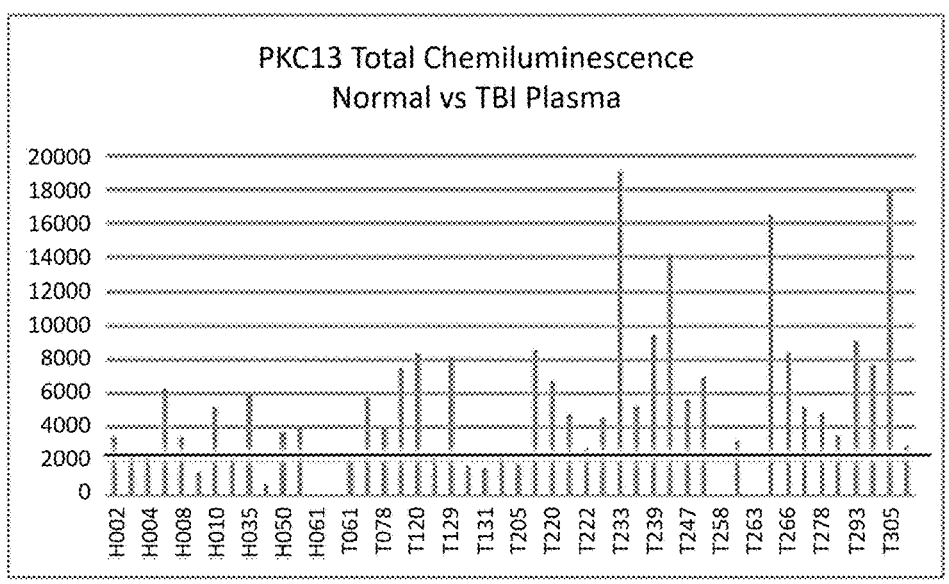
Figure 2C:
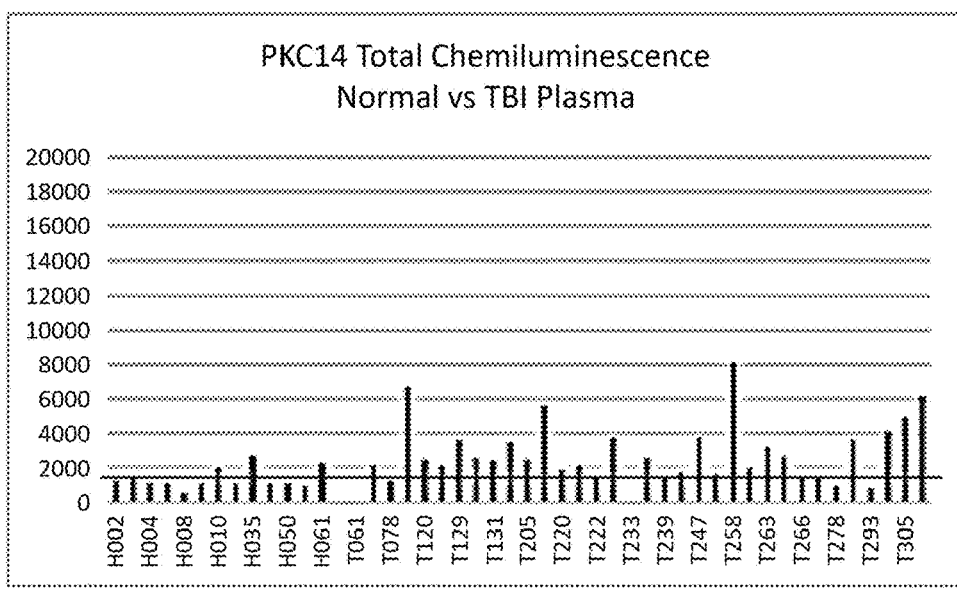

Staining patterns for individual samples probed with the anti-PKCg mAbs are shown in FIG. 2. Normal human plasma samples, (n=13 individuals), were compared to Traumatic Brain Injury samples, (n=34 individuals), stained with antibodies PKC11 (panel A), PKC13 (panel B), and PKC14 (panel C).

Staining patterns with PKC11, PKC13, and PKC14 are unique. High peaks in PKC11 TBI samples (T) include T130, T223, T247 vs. PKC13 peaks at T220, T233, T240, T265, T266, T293, T305 and PKC14 peaks at T079, T209, T258. A positive diagnosis of TBI was made for PKC11 in 91% of the samples (30/33 TBI samples above the background), 91% of the samples for PKC13 (31/34 TBI samples positive) and 91% of the samples for PKC14 (30/33 TBI samples positive).

Multiplex Analysis of TBI Samples

Figure 3:
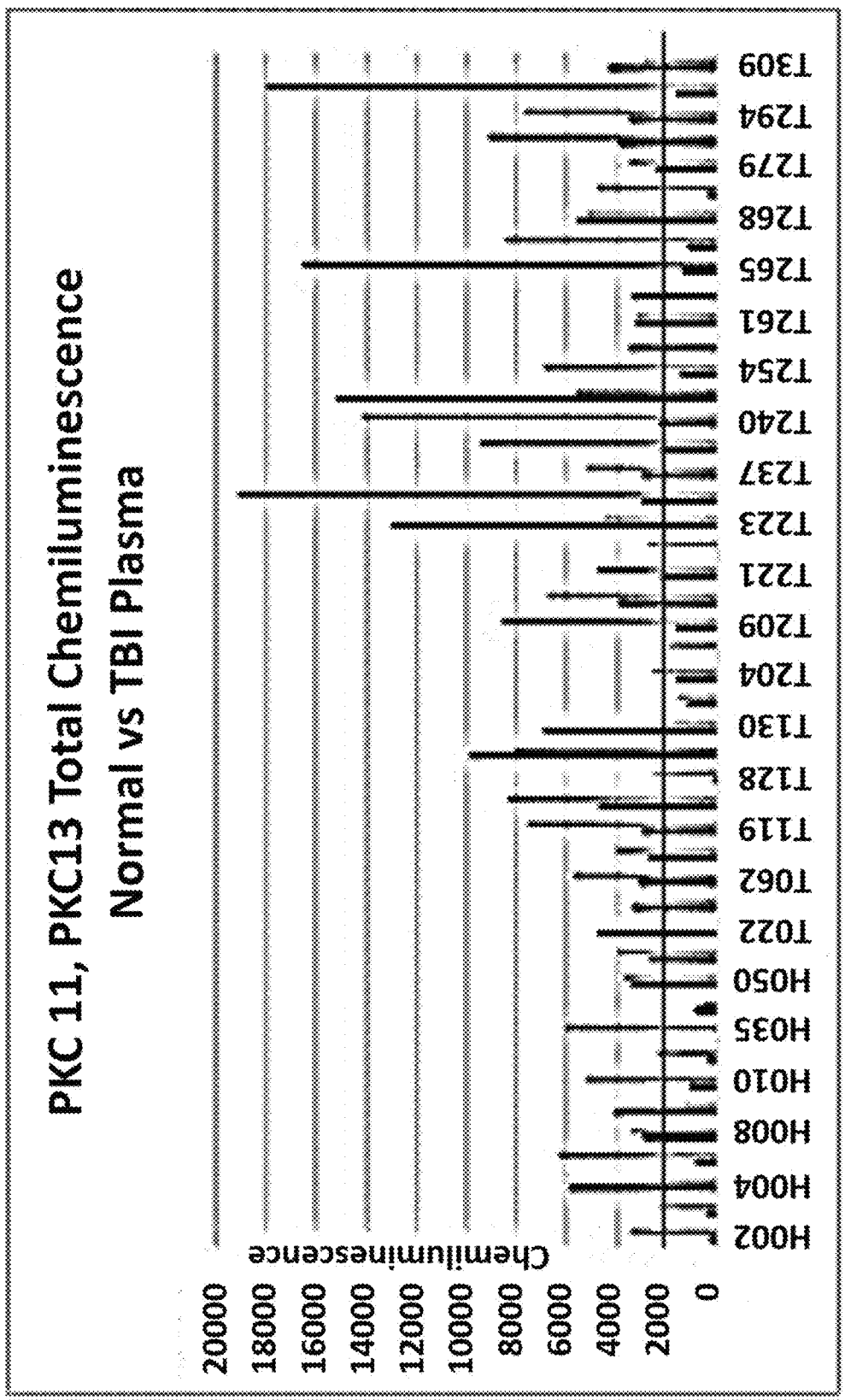
FIG. 3 is a multiplex analysis using two monoclonal antibodies, PKC11 (1H1/1K1) and PKC13 (5H1/5K1) staining of normal vs. TBI plasma samples.

As demonstrated below, it was discovered that by combining (also referred to herein as "multiplexing") the chemiluminescent binding results for two monoclonal antibodies for PKCg leads to a marked improvement in the accuracy and reliability of TBI diagnosis. The results of multiplexing the PKCg binding results of antibodies PKC11 and PKC13 for the TBI samples are shown in FIG. 3 with PKC11 shown as black vertical lines and PKC13 shown as gray vertical lines.

PKC11 and PKC13 were multiplexed to determine the resulting effects on a positive diagnosis of TBI. Combining the chemiluminescent results for PKC11 and PKC13 improved the TBI-positive diagnosis from 91% when antibodies were assessed individually to 100% TBI-positive for the combined antibodies (34/34 TBI(+) samples at or above the background line). Multiplexing with PKC14 did not further improve this (100% accurate) diagnosis (data not shown).

PKC11 and PKC13 antibody stains of normal human plasma vs. TBI plasma samples were plotted concurrently illustrating the differences in staining between the two antibodies. For some samples, e.g., T022, T130, and T223, the mAb PKC11 chemiluminescent signal exceeded the mAb PKC13 signal; but for TBI samples T265 and T266, a very high signal was shown, as compared with a low signal for the same samples stained with mAb PKC11. The horizontal cut-off (line) in FIG. 3 is 1137 chemiluminescent units derived from the ROC Curve fit analysis of PKC11+PKC13 multiplexed antibodies. Any signal higher than this level represents a predicted TBI(+) sample based on the detection of antibody binding to target PKCg and PKCg proteolytic fragment target biomarkers. The addition of mAb PKC14 to the multiplex of mAb PKC11 and mAb PKC13 did not improve ROC Curve analysis or the diagnosis of TBI-positive samples (data not shown).

Analysis of TBI Vs. Normal Plasma Samples Stained with Anti-PKCg mAbs

Figure 4A:
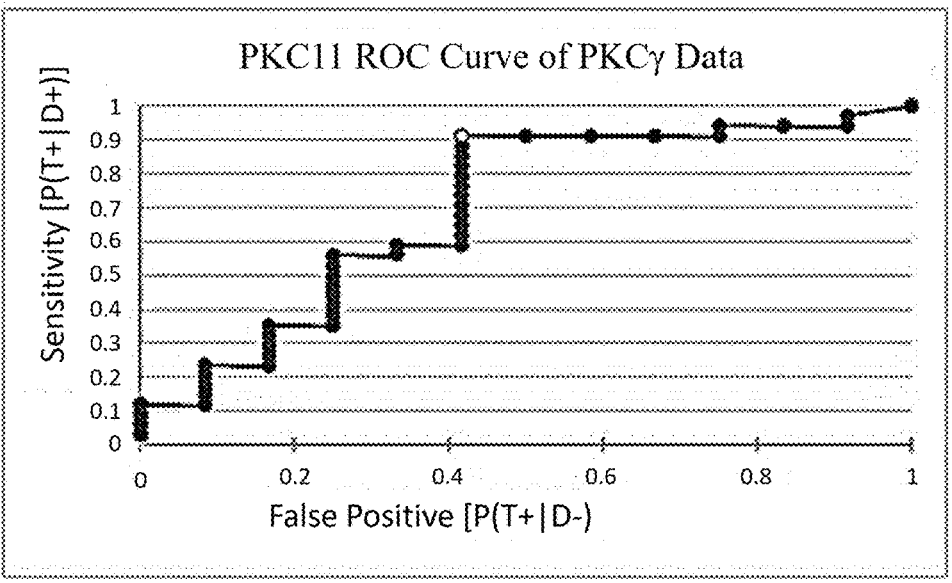
FIGS. 4A, 4B, and 4C show the ROC Curves of TBI vs. normal plasma stained with PKC11 (panel A), PCK13 (panel B), and PKC14 (panel C). The white dot in FIGS. 4A, 4B, and 4C represents the point where sensitivity and false positives was calculated: (A) Chemiluminescence 1137; Sensitivity of P=0.91 with a False Positive of P=0.4; (B) Chemiluminescence 6630; Sensitivity of P=0.91 with a False Positive of (P=0.58); (C) Chemiluminescence 1320; Sensitivity of P=0.906 with a False Positive of P=0.66).
Figure 4B:
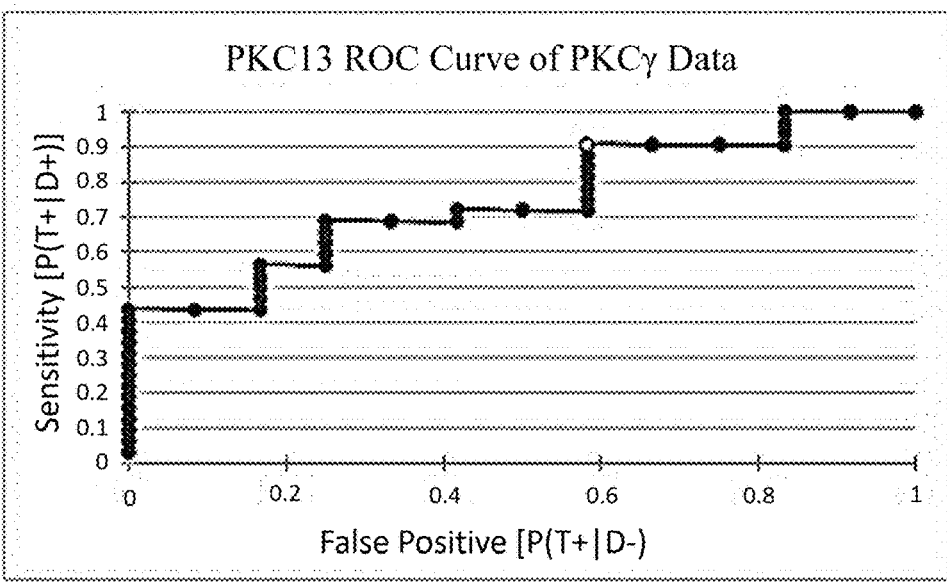
Figure 4C:
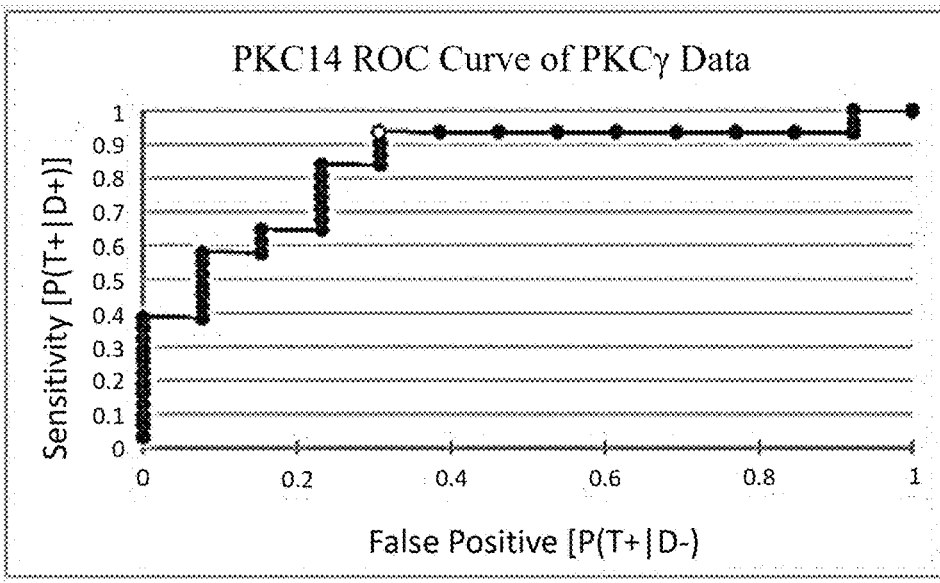

Plasma samples from normal and TBI patients were stained with the PKC11, PKC13, or PKC14 monoclonal antibodies and analyzed for the presence of PKCg and PKCg proteolytic fragments by the chemiluminescence assay described above. The ROC Curve results for TBI vs. normal plasma samples are shown in FIGS. 4A-4C. Several subsets of normal vs. TBI samples were run which generated some repeat measures making the final tally of 145 TBI samples analyzed.

The results shown in FIG. 4 demonstrate that all three antibodies reached a sensitivity higher than 91% with different specificities and false positives. PKC11 (panel A) had Sensitivity of 91%, Specificity of 58%, and 42% False Positives. PKC13 (panel B) exhibited Sensitivity of 91%, Specificity of 42% and the highest false positives at 58%. PKC14 (panel C) showed a Sensitivity of 94%, Specificity of 70%, and False positives at 30%.

The consequence to a patient showing a false positive probability is the patient would need to undergo additional blood draw and re-testing of the PKCg assay to confirm the PKCg levels in the sample. This is a significant factor in a diagnosis setting where time is of the essence for prescribing effective treatment to attenuate the effect of CNS injury. With further indication of higher than normal levels of PKCg, the patient would undergo neurological and interventional radiology testing to identify additional clinical concerns for the patient. The clinical benefit of rapid and accurate diagnosis of TBI is lost if the incidence and probability of false positives is high. This makes TBI diagnostic assays of improved sensitivity highly desirable.

Detection of PKCg/PKCg Proteolytic Fragments by Antibodies PKC11, PKC13, and PKC14

Figure 5:
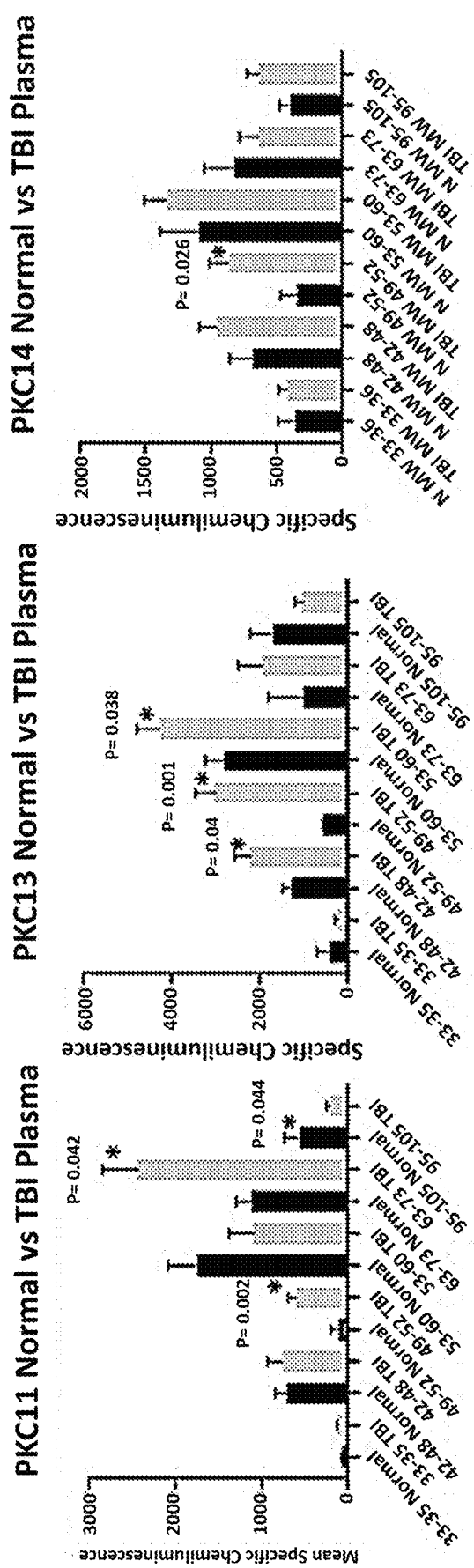
FIG. 5 is a statistical comparison of chemiluminescent signals of the normal and TBI samples stained with PKC11

A statistical comparison of chemiluminescent signals of normal and TBI samples stained with PKC11, PKC13, and PKC14 was conducted. The results are shown in FIG. 5. A statistical comparison is an unpaired, two tailed Student T-test (GraphPad Prism 8). The graphs in FIG. 5 represent the mean and SE of the mean; * represents significance at the 95% confidence level and p values are listed for significant measures. As seen in FIG. 5, each monoclonal antibody shows a unique staining pattern for normal and TBI plasma. The 49-52 kDa fragment of PKCg is prevalent for all three antibodies which improves the TBI(+) diagnosis. All three antibodies show detection of significantly higher levels of the 49-52 kDa fragment in TBI samples as compared with normal plasma.

The PKC11 antibody shows a significant increase in the signal for TBI plasma compared to normal plasma for the 49-52 kDa fragment, and PKC11 shows the highest signal for full-length PKCg (63-73 kDa) in TBI plasma compared against samples of normal plasma.

The PKC13 antibody shows the greatest signal response to binding PKCg/PKCg fragment targets. PKC13 has a significant signal increase for the 42-48 kDa, 49-52 kDa, and 53-60 kDa fragments, which improves the TBI(+) diagnosis.

The PKC14 antibody has a significant signal increase for detection of the 49-52 kDa fragment. The highest signal was for the 53-60 kDa fragment, but the signal for the 42-48 kDa fragment was not significantly different for the normal vs. TBI samples.

Comparison of Antibody Stained Bands in Normal Vs. TBI Plasma Samples

FIG. 6 shows a typical differential distribution of PKCg and PKCg proteolytic fragments recognized by PKC13 in a normal human plasma sample (H011) (top panel) compared to a plasma sample from a TBI patient (T265) (bottom panel).

The results in FIG. 6 demonstrate that in normal human plasma samples the presence of the 49-52 kDa fragment is extremely rare. In contrast, PKC13 detects the 49-52 kDa fragment in high levels in TBI plasma thereby enhancing the ability to make a TBI(+) diagnosis.

Receiver Operator Curve (ROC) Fragment 49-52 KD Stained with PKC11, PKC13, and PKC14

ROC Curves were generated for the PKCg 49-52 kDa fragment stained with rabbit monoclonal antibodies PKC11 (A), PKC13 (B), and PKC14 (C). The results are shown in FIGS. 7A, 7B, and 7C.

The black circles in FIG. 7 represent TBI plasma samples. The white circles represent the maximal sensitivity without any false positives. Gray circles represent false positives, i.e., normal plasma samples with a positive response for the PKCg 49-52 kDa fragment.

In FIG. 7A, the ROC Curve of samples stained with PKC11 having a chemiluminescence signal at or higher than 710 units (white circle) are TBI-positive. There are no false positives up to this point (Sensitivity of P=0.64, False Positives P=0.0, and Specificity of P=1.0), however at a signal of 630 chemiluminescence units there is one false positive. This is the only normal (or non-TBI) human plasma sample that stained positive for the PKCg 49-52 kDa fragment under these conditions. Additional testing may show this sample is in fact a sample positive for CNS injury. This would move the sensitivity to greater than P=0.9, as in curves B and C.

FIG. 7B represents PKC13 staining of the PKCg 49-52 kDa fragment for normal human plasma compared to TBI plasma. The white circle identifies the point at which a sample signals at or greater than 658 chemiluminescence units and are a TBI(+) sample. The Sensitivity at this point is P=0.95, Specificity is P=1.0, and False Positives at P=0.0. There is only one TBI-positive sample identified at a signal lower than the 2 normal human plasma samples. Two false positive normal plasma sample were identified (gray circles) at 582 and 579 chemiluminescence units. Corresponding Sensitivity is P=0.95 while False Positives rise to a probability of P=0.5 and P=1.0 for these 2 points.

FIG. 7C represents PKC14 staining of the PKCg 49-52 kDa fragment for normal human plasma compared to TBI plasma. The white circle identifies a sample signal of 299 chemiluminescence units; any sample with a signal at or higher than this is identified as TBI-positive. At this point the Sensitivity is P=0.92, with False Positives P=0 and Specificity P=1.0. There are three False Positive samples with lower chemiluminescence signals (gray circles) and an additional TBI(+) sample. For these additional points the Sensitivity goes up to P=1.0 and False Positives rises to a probability of P=0.33.

Conclusions for TBI

The data presented above demonstrate that the novel in vitro method of the present invention provides a simple, quick, and reliable tool for diagnosing a traumatic brain injury from a sample of venous blood. Using a standard assay, such as the capillary chemiluminescence assay described above, it has been demonstrated that all of the three rabbit monoclonal antibodies described above, PKC11, PKC13, and PKC14, recognize unique epitopes on the PKCg/PKCg proteolytic fragment biomarkers for CNS injury, and each antibody displays a unique staining pattern for these biomarkers and thereby, when used individually or in combination, provide a reliable diagnostic tool for determining the occurrence and severity of a traumatic brain injury.

The results also demonstrate that the 49-52 kDa fragment is usually found only in TBI(+) samples and as such the PKCg or PKCg fragment improves the diagnosis of TBI in subjects tested according to the method of the invention. The Sensitivity of the 49-52 kDa fragment analyzed by ROC Curves is greater than probability P=0.91 for all three monoclonal antibodies studied, making it an ideal amplifier of the diagnosis of clinical TBI.

Additional fragments, such as the 33-36 kDa, 42-48 kDa, 53-60 kDa fragments have a lower Sensitivity than the 49-52 kDa fragment by ROC analysis (P=<0.9) with corresponding elevated probabilities of False Positives. These additional fragments therefore enhance the diagnosis of TBI to a lesser degree in samples stained with the three monoclonal antibodies but still provide a useful and reliable indicator of TBI. Furthermore, the combination of any two of the anti-PKCg antibodies recognizing one or more typical PKCg proteolytic fragments improves the accuracy of the diagnosis to 100%.

Example 3. Analysis of Anti-PKCg Monoclonal Antibody Binding to PKCg Proteolytic Fragments in Diagnosing Stroke from Human Plasma Samples Plasma samples from subjects having been diagnosed as suffering a stroke were analyzed for the presence of PKCg and PKCg proteolytic fragments by staining with mAbs PKC11, PKC13, and PKC14 according to the chemiluminescence capillary ELISA assay as described above. The results demonstrate that the novel method of the present invention provides a quick and reliable diagnostic method for detecting stroke in patients suspected of suffering therefrom.

Detection of PKCg in Normal Vs. Stroke Plasma Samples

Staining of the stroke samples with PKC11, PKC13, and PKC14 using the chemiluminescence capillary assay showed significantly higher levels of PKCg in stroke vs. normal human plasma samples. FIG. 8 shows the aggregate signals from all contributing samples of stroke vs. normal samples stained with each monoclonal antibody (PKC11, PKC13, and PKC14). As demonstrated above for the TBI plasma samples, each monoclonal antibody shows a unique staining pattern.

Detection of PKCg using Multiplexed Antibodies

Plasma samples from the stroke patients were analyzed for the presence of PKCg and PKCg proteolytic fragments by staining with the PKC11 and PKC13 monoclonal antibodies individually and multiplexed (both PKC11 and PKC13) according to the chemiluminescence capillary ELISA assay as described above. The results are shown in FIGS. 9A-9C. S-numbered samples were obtained from stroke patients; H-numbered samples were obtained from normal (non-stroke) individuals.

The results demonstrate that the novel method of the present invention provides a quick and reliable diagnostic method for detecting the occurrence of a stroke in patients having suffered a stroke event. Further, the results again indicate that multiplexing with anti-PKCg antibodies having different PKCg fragment specificities improves the certainty of this diagnosis.

PKC11 staining of individual samples of normal human plasma compared against plasma samples of stroke victims in FIG. 9A shows 7/10 positive stroke samples greater than the baseline (70% detection). PKC13 staining shown in FIG. 9B shows 9 stroke samples above the line (9/11, or 82% detection). When PKC11 and PKC13 are multiplexed, as shown FIG. 9C, an increase in detection of positive stroke diagnosis is calculated with 10 Stroke samples above the line (10/11, or 91% detection). FIGS. 9A and 9B show different chemiluminescence patterns, such as the high positive signal in sample S013 in FIG. 9A and the high positive signal in sample S017 in FIG. 9B. Therefore, by combining the sensitivity and specificity of mAbs PKC11 and PKC13 in an assay, stroke diagnosis accuracy improves to 91%. The horizontal baseline in FIG. 9 represents 3445 chemiluminescence units.

Detection of PKCg Fragments in Normal Vs. Stroke Plasma Samples

A statistical comparison of chemiluminescent signals of normal and stroke plasma samples stained with PKC11, PKC13, and PKC14 was conducted. The results are shown in FIGS. 10A-10C. A statistical comparison is an unpaired, two-tailed Student T-test (using GraphPad Prism 8). The graphs in FIG. 10 represent the mean and SE of the mean; * represents significance at the 95% confidence level and p values are listed for significant measures.

FIG. 10A shows a higher peak at the 63-73 kDa and 49-52 kDa PKCg fragments for stroke samples contacted with mAb PKC11, however these differences are not statistically significant when compared to normal human plasma. There is a significant peak for the 53-60 kDa fragment of PKCg in normal plasma samples when compared to stroke plasma samples stained with PKC11.

FIG. 10B shows a significant increase in the presence of the 42-48 kDa PKCg fragment in stroke samples vs. control plasma (P=0.038) stained with mAb PKC13. The 49-52 kDa fragment is higher in stroke plasma and is nearly significant (P=0.06) when compared to normal plasma samples. Presumably a larger sample number would present with a significant increase in stroke(+) samples for the PKCg 49-52 kDa fragment. The higher molecular weight band at 95-105 kDa is significant in the stroke samples when compared to normal plasma in the PKC13-stained samples. No 63-73 kDa fragments are evident in stroke samples stained with PKC13.

FIG. 10C shows staining of normal human plasma vs. stroke plasma probed with mAb PKC14. This antibody shows no significantly differential staining bands and has a lower signal than the other two antibodies tested.

Detection of the PKCg 49-52 kDa Fragments in Normal Vs. Stroke Plasma Samples

FIGS. 11A-11C show the ROC Curve analyses of the PKCg 49-52 kDa fragment in normal vs. stroke plasma samples stained with PKC11 (panel A), PKC13 (panel B), and PKC14 (panel C), respectively.

The ROC curve analysis shows high Sensitivity of individual 49-52 kDa fragments from normal vs. stroke plasma samples stained with PKC11, PKC13, and PKC14, which confirms the enhanced diagnostic utility of the assaying for the PKCg 49-52 kDa proteolytic fragment for diagnosing stroke. The analysis shown in FIG. 11A is for only a few examples (n=3), however the sensitivity remains high (P=1.0) with no false positives (P=0). The white circle identifies stroke-positive samples at a signal greater than 797 chemiluminescence units stained with PKC11. The gray circle represents a healthy control at 602 chemiluminescence units.

For PKC13 staining of the 49-52 kDa fragment, shown in FIG. 11B, the Sensitivity also remains high (P=1.0) with no false positives (P=0) and Specificity (P=1.0). The white circle represents 999 chemiluminescence units; any signal greater than this represents a stroke-positive sample. There are 2 healthy control samples with signals at 582 and 579 chemiluminescence units (gray circles).

The results for PKC14 staining of the 49-52 kDa fragment, shown in FIG. 11C, again confirms the suitability of this fragment as an important diagnostic target for diagnosing stroke. The sensitivity of the assay remains very high (P=1.0) with 0 false positives (Specificity P=1.0) even though the overall composite signal from each of the fragments is low (Cf. FIG. 10). The white circle is at 257 chemiluminescence units, a signal higher than this represents a stroke-positive sample. Healthy (non-stroke) plasma samples (gray circles) have lower chemiluminescence signals than for the white circle.

Detection of PKCg Alternate Fragments in Normal Vs. Stroke Plasma Samples

An analysis of stroke samples compared with normal human plasma samples illustrates the degree that PKCg fragments can contribute to a stroke-positive diagnosis. The ROC analysis of the PKCg 33-36 kDa, 42-48 kDa, and 53-60 kDa fragments stained with PKC11, PKC13, and PKC14 do not reach the Sensitivity seen for the 49-52 kDa fragment (P>0.9) and as such contribute varying degrees of enhancement to the diagnosis of stroke. The results are shown in Table 3 (below).

For example, PKC13 staining shows Sensitivity in the range of P=0.7 to P=0.8 with False Positives less than or equal to P=0.2 and Specificity P=0.8 to P=1.0. The contributions to the signal for the 42-48 kDa and 53-60 kDa fragments are greater than 2200 chemiluminescence units with the probability of false positives at a low level (20%).

Another example from Table 3 shows that the major contribution of stroke diagnosis for the 63-73 kDa fragment is from PKC11 with Sensitivity at P=0.5, False Positives at P=0.3 and Specificity at P=0.7. In contrast, PKC13 shows no response for the 63-73 kDa fragment. (See, Table 3). PKC14 shows a response for the 63-73 kDa fragment with a signal of 688 chemiluminescence units but lower Sensitivity and higher False Positives (Sensitivity P=0.5 and False Positives P=0.5).

TABLE 3

ROC Analysis of Various PKCg Fragments in Stroke vs. Normal Human Plasma

| PKCg Antibody | Fragment (Name) | Sensitivity P = | False Positive P = | Signal Chemiluminescence |
|---|---|---|---|---|
| PKC11 | 33-36 kDa | 0.75 | 0.2 | 126 |
|  | 42-48 kDa | 0.33 | 0.6 | 637 |
|  | 53-60 kDa | 0.33 | 0.54 | 1545 |
|  | 63-73 kDa | 0.5 | 0.33 | 1770 |
| PKC13 | 33-36 kDa | 0.71 | 0.2 | 319 |
|  | 42-48 kDa | 0.8 | 0 | 2213 |
|  | 53-60 kDa | 0.78 | 0.2 | 3348 |
|  | 63-73 kDa | No Response |  |  |
| PKC14 | 33-36 kDa | 0.78 | 0.42 | 230 |
|  | 42-48 kDa | 0.88 | 0.33 | 633 |
|  | 53-60 kDa | 0.6 | 0.36 | 654 |
|  | 63-73 kDa | 0.5 | 0.5 | 866 |
|  | 95-105 | 0.63 | 0.33 | 443 |

Therefore, signals from the PKCg fragments with high Sensitivity, High Specificity, and Low False Positives, are shown to enhance the stroke(+) diagnosis.

ROC Curve for the PKCg 42-48 kDa Fragment in Normal Vs. Stroke Plasma Samples Stained with mAb PKC13

FIG. 12 shows the ROC Curve analysis of the normal vs. stroke samples stained with PKC13 for the 42-48 kDa PKCg fragment. Staining of the PKCg 42-48 kDa fragment with PKC13 shows 0 False Positives at a Sensitivity of P=0.8 and Specificity of P=1.0. The black dots in FIG. 12 represent stroke(+) plasma samples, while gray dots represent normal healthy controls. The white dot corresponds to a chemiluminescence signal of 2213. Samples with signals at or above 2213 Chemiluminescence units are considered positive for the stroke diagnosis. Signals from PKCg fragments such as PKC13 staining of the 42-48 kDa fragment has relatively high Sensitivity, high Specificity and low False Positives, which enhances the accuracy of stroke(+) diagnosis.

CONCLUSIONS

All rabbit monoclonal antibodies recovered have different variable region sequences and bind to different epitopes on the PKCg protein. Three of the rabbit monoclonal antibodies cloned, i.e., PKC11, PKC13, and PKC14, were analyzed for the ability to detect PKCg and PKCg proteolytic fragments in plasma samples of patients diagnosed as having suffered a TBI and patients diagnosed with having suffered a stroke, compared with plasma samples from normal (control) subjects, using quantitative chemiluminescence capillary Western blot techniques.

Rabbit monoclonal antibodies PKC11, PKC13, and PKC14 can bind to unique epitopes present on the full-length PKCg protein. In addition, all three rabbit monoclonal antibodies recognize epitopes present on the PKCg proteolytic fragments of 32-36 kDa, 42-48 kDa, 49-52 kDa, and 53-60 kDa that develop as a result of CNS injury and transport across the BBB in peripheral circulation.

PKC11 and PKC13 show strong signals (binding to) for full-length PKCg and the PKCg proteolytic fragments. Multiplexing of PKC11 and PKC13 antibodies for the PKCg proteolytic fragments greatly enhances the diagnosis of TBI or stroke in plasma samples. Analysis of the proteolytic fragments of PKCg combined from PKC11, PKC13, and PKC14 staining can improve the detection rate (diagnosis) to varying degrees of both TBI and stroke in the clinical samples tested. In particular, the presence of the PKCg 49-52 kDa fragment in a sample greatly enhances the diagnosis of both TBI(+) and stroke(+) because it is rarely found in normal human plasma and presents with high Sensitivity, low False Positives, and high Specificity in both TBI and stroke samples.

Therefore, as described above, the novel in vitro method of the present invention for detecting and quantifying the presence of PKCg proteolytic fragments and PKCg from a venous blood sample is capable of rapidly and reliably diagnosing the occurrence of a CNS injury such as traumatic brain injury or stroke in an affected individual. The present invention also provides unique monoclonal antibodies particularly suited for use in the novel in vitro methods for diagnosing TBI and stroke, which antibodies recognize (and form a detectable binding complex with) at least one epitope present on the full length PKCg protein and recognize (and form a binding complex with) at least one unique epitope present on at least one of the PKCg proteolytic fragments described above, which binding complexes may be detected by any process known in the art for detecting biomarkers in a biological sample.

The publications, patent applications, patents, and other documents cited herein are incorporated by reference in their entirety. The examples set forth above are illustrative only and are not intended to be limiting. Obvious variations to the disclosed methods and alternative embodiments of the invention will be apparent to those skilled in the art in view of the foregoing disclosure. All such obvious variants and alternatives are considered to be within the scope of the invention as described herein. pq,43

---

The invention claimed is:

1. An antibody, or antigen-binding portion thereof, comprising SEQ ID NO: 3, SEQ ID NO: 4, SEQ ID NO: 5, SEQ ID NO: 6, SEQ ID NO: 7, and SEQ ID NO: 8 or comprising SEQ ID NO: 9, SEQ ID NO: 10, SEQ ID NO: 11, SEQ ID NO: 12, SEQ ID NO: 13, and SEQ ID NO: 14, or comprising SEQ ID NO: 15, SEQ ID NO: 16, SEQ ID NO: 17, SEQ ID NO: 18, SEQ ID NO: 19, and SEQ ID NO: 20.

2. The antibody, or antigen-binding portion thereof, of claim 1 comprising SEQ ID NO: 21 and SEQ ID NO: 22, or comprising SEQ ID NO: 32 and SEQ ID NO: 33 or comprising SEQ ID NO: 25 and SEQ ID NO: 26.

3. An in vitro method for diagnosing a traumatic brain injury or a stroke comprising:
   a) contacting a sample of blood from a subject suspected of having a traumatic brain injury or stroke with a first antibody having an antigen-binding portion comprising SEQ ID NO: 3, SEQ ID NO: 4, SEQ ID NO: 5, SEQ ID NO: 6, SEQ ID NO: 7, and SEQ ID NO: 8, and a second antibody having an antigen-binding portion comprising SEQ ID NO: 9, SEQ ID NO: 10, SEQ ID NO: 11, SEQ ID NO: 12, SEQ ID NO: 13, and SEQ ID NO: 14, and
   b) detecting the formation of a binding complex of the first antibody to an epitope, and detecting the formation of a binding complex of the second antibody to an epitope, wherein the detection of the binding complexes indicates a traumatic brain injury or stroke.

4. The method of claim 3 wherein the first antibody comprises SEQ ID NO: 21 and SEQ ID NO: 22 and wherein the second antibody comprises SEQ ID NO: 32 and SEQ ID NO: 33.

5. The method of claim 3 further comprising contacting the sample of blood from a subject suspected of having a traumatic brain injury or stroke with a third antibody having an antigen-binding portion comprising SEQ ID NO: 15, SEQ ID NO: 16, SEQ ID NO: 17, SEQ ID NO: 18, SEQ ID NO: 19, and SEQ ID NO:20, and detecting the formation of a binding complex of the third antibody to an epitope.

6. The method of claim 5 wherein the third antibody comprises SEQ ID NO: 25 and SEQ ID NO: 26.

* * * * *